(12) United States Patent
Cerutti et al.

(10) Patent No.: US 12,385,014 B2
(45) Date of Patent: Aug. 12, 2025

(54) BACULOVIRUS EXPRESSION SYSTEM

(71) Applicants: CENTRE NATIONAL DE LA RECHERCHE SCIENTIFIQUE (CNRS), Paris (FR); INSTITUT NATIONAL DE LA RECHERCHE AGRONOMIQUE, Paris (FR)

(72) Inventors: Martine Cerutti, Saint Christol les Ales (FR); Sylvie Juliant, Saint Christol les Ales (FR); Sylvie Thery, Saint Martin de Valgalgues (FR)

(73) Assignees: CENTRE NATIONAL DEL LA RECHERCH SCIENTIFIQUE (CNRS), Paris (FR); INSTITUT NATIONAL DE LA RECHERCHE AGRONOMQIUE, Paris (FR)

( * ) Notice: Subject to any disclaimer, the term of this patent is extended or adjusted under 35 U.S.C. 154(b) by 851 days.

(21) Appl. No.: 16/321,634

(22) PCT Filed: Aug. 4, 2017

(86) PCT No.: PCT/FR2017/052191
§ 371 (c)(1),
(2) Date: Jan. 29, 2019

(87) PCT Pub. No.: WO2018/024998
PCT Pub. Date: Feb. 8, 2018

(65) Prior Publication Data
US 2023/0063208 A1    Mar. 2, 2023

(30) Foreign Application Priority Data
Aug. 5, 2016 (FR) .................................... 1657611

(51) Int. Cl.
C12N 7/00 (2006.01)
C12N 15/86 (2006.01)
C12N 15/90 (2006.01)

(52) U.S. Cl.
CPC ............... *C12N 7/00* (2013.01); *C12N 15/86* (2013.01); *C12N 15/902* (2013.01); *C12N 2710/14151* (2013.01)

(58) Field of Classification Search
CPC ........ C12N 7/00; C12N 15/86; C12N 15/902; C12N 2710/14151
See application file for complete search history.

(56) References Cited

U.S. PATENT DOCUMENTS 9,212,374 B2 * 12/2015 Roy ........................ C12N 15/63
2023/0063208 A1    3/2023 Cerutti et al.

FOREIGN PATENT DOCUMENTS

WO    2001012829 A2    2/2001
WO    WO-0112829 A2 *  2/2001 ........... C07K 14/005
WO    2010055292 A2    5/2010
WO    2013005194       1/2013
WO    2018024998       2/2018

OTHER PUBLICATIONS

Weyer U, Possee RD. A baculovirus dual expression vector derived from the Autographa californica nuclear polyhedrosis virus polyhedrin and p10 promoters: co-expression of two influenza virus genes in insect cells. J Gen Virol. Dec. 1991;72 ( Pt 12):2967-74. (Year: 1991).*
St Angelo C, Smith GE, Summers MD, Krug RM. Two of the three influenza viral polymerase proteins expressed by using baculovirus vectors form a complex in insect cells. J Virol. Feb. 1987;61(2):361-5. doi: 10.1128/JVI.61.2.361-365.1987. (Year: 1987).*
Je et al. Generation of Baculovirus Expression Vector Using Defective Autographa californica Nuclear Polyhedrosis Virus Genome Maintained in *Escherichia coli* for Occ+ Virus Production. Int. J. Indust. Entomol. pp. vol. 2, No. 2, 2001, (Year: 2001).*
Van Oers MM. Opportunities and challenges for the baculovirus expression system. J Invertebr Pathol. Jul. 2011;107 Suppl:S3-15. (Year: 2011).*
Gay et al., "Insertion of transposon Tn7 into the *Escherichia coli* glmS transcriptional terminator," Biochem J., 234:111-117 (1986).
Drocourt et al., "Chemical synthesis and biological activities of analogues of 2',5'-oligoadenylates containing 8-substituted adenosine derivatives," Nucleic Acids Research, 18(13):4439-4446 (1990).
Gentz et al., "Promoters Recognized by *Escherichia coli* RNA Polymerase Selected by Function: Highly Efficient Promoters from Bacteriophage T5," J. Bacteriology, 164(1):70-77 (1985).
Kwon et al, "Bipartite Modular Structure of Intrinsic, RNA Hairpin-independent Termination Signal for Phage RNA Polymerases" J Biol. Chem., 274(49):34940-34947 (1999).
Kanai et al., "Multiple large foreign protein expression by a single recombinant baculovirus: A system for production of multivalent vaccines," Protein Expression and Purification, 91:77-84 (2013).
Possee et al., "Generation of Baculovirus Vectors for the High-Throughput Production of Proteins in Insect Cells," Biotechnology and Bioengineering, 101(6):1115-1122 (2008).
Poul et al., "Design of cassette baculovirus vectors for the production of therapeutic antibodies in insect cells," Immunotechnology, 1(3):189-196 (1995).
Vijayachandran et al., "Gene gymnastics," Bioengineered, 4(5):279-287 (2013).

(Continued)

*Primary Examiner* — Nicole Kinsey White
*Assistant Examiner* — Ruixue Wang
(74) *Attorney, Agent, or Firm* — Arrigo, Lee, Guttman & Mouta-Bellum, LLP; Carla Mouta-Bellum

(57) ABSTRACT

The invention relates to a method for producing a recombinant baculovirus comprising n exogenous genes in an insect cell, by means of homologous recombination of a replication-deficient baculovirus genome and n transfer vectors, each comprising one of the n exogenous genes, n being an integer at least equal to 2.

Figure 2:
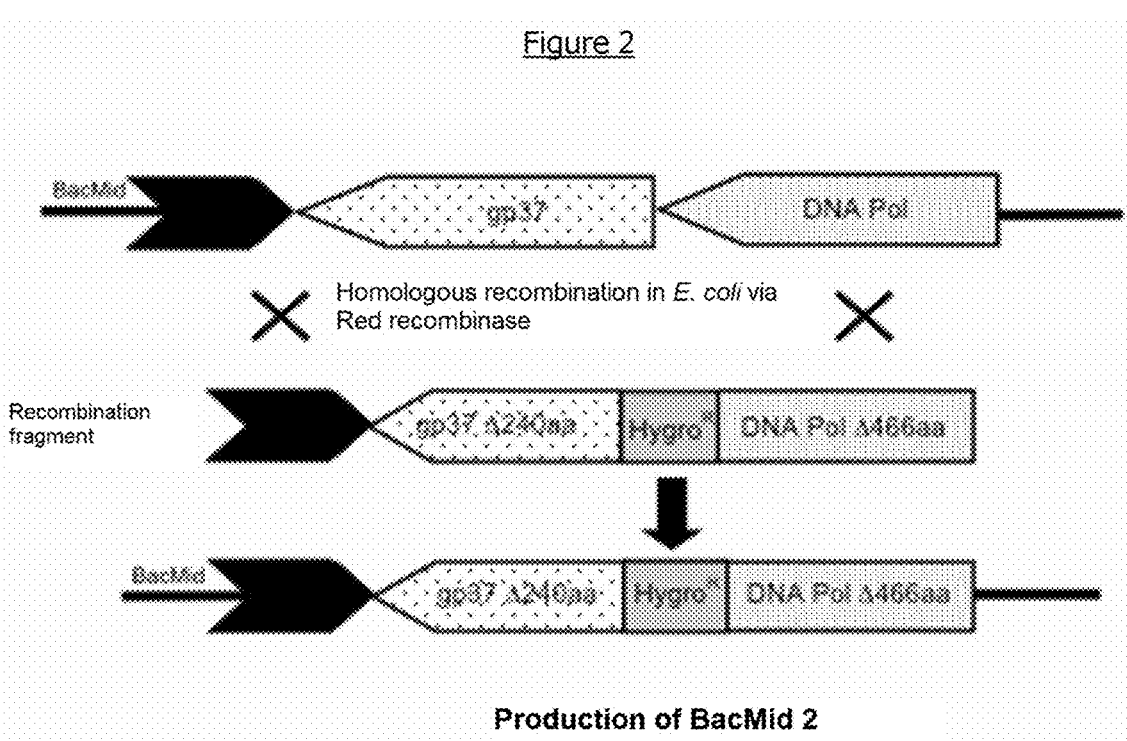

10 Claims, 11 Drawing Sheets
Specification includes a Sequence Listing.

(56) References Cited

OTHER PUBLICATIONS

Pijlman et al., "Spontaneous excision of BAC vector sequences from bacmid-derived baculovirus expression vectors upon passage in insect cells," Journal of General Virology, 84(10):2669-2678 (2003).
Palmberger D, Wilson IB, Berger I, Grabherr R, Rendic D. SweetBac: a new approach for the production of mammalianised glycoproteins in insect cells. PLoS One. 2012;7(4):e34226.
Chang GD, Chen CJ, Lin CY, Chen HC, Chen H. Improvement of glycosylation in insect cells with mammalian glycosyltransferases. J Biotechnol. Apr. 10, 2003;102(1):61-71.
Possee RD, Hitchman RB, Richards KS, Mann SG, Siaterli E, Nixon CP, Irving H, Assenberg R, Alderton D, Owens RJ, King LA. Generation of baculovirus vectors for the high-throughput production of proteins in insect cells. Biotechnol Bioeng. Dec. 15, 2008;101(6):1115-22.
Tan J, D'Agostaro AF, Bendiak B, Reck F, Sarkar M, Squire JA, Leong P, Schachter H. The human UDP-N-acetylglucosamine: alpha-6-D-mannoside-beta-1,2-N-acetylglucosaminyltransferase II gene (MGAT2). Cloning of genomic DNA, localization to chromosome 14q21, expression in insect cells and purification of the recombinant protein. Eur J Biochem. Jul. 15, 1995;231(2):317-28.
D'Agostaro G, Bendiak B, Tropak M. Cloning of cDNA encoding the membrane-bound form of bovine beta 1,4- galactosyltransferase. Eur J Biochem. Jul. 15, 1989;183(1):211-7.
Munster AK, Eckhardt M, Potvin B, Mühlenhoff M, Stanley P, Gerardy-Schahn R. Mammalian cytidine 5'-monophosphate N-acetylneuraminic acid synthetase: a nuclear protein with evolutionarily conserved structural motifs. Proc Natl Acad Sci U S A. Aug. 4, 1998;95(16):9140-5.
Lawrence SM, Huddleston KA, Pitts LR, Nguyen N, Lee YC, Vann WF, Coleman TA, Betenbaugh MJ. Cloning and expression of the human N-acetylneuraminic acid phosphate synthase gene with 2-keto-3-deoxy-D-glycero-D-galacto-nononic acid biosynthetic ability. J Biol Chem. Jun. 9, 2000;275(23):17869-77.
Kitagawa H, Paulson JC. Cloning of a novel alpha 2,3-sialyltransferase that sialylates glycoprotein and glycolipid carbohydrate groups. J Biol Chem. Jan. 14, 1994;269(2):1394-401.
Grundmann U, Nerlich C, Rein T, Zettlmeissl G. Complete cDNA sequence encoding human beta-galactoside alpha-2,6-sialyltransferase. Nucleic Acids Res. Feb. 11, 1990;18(3):667.
Cieplik M, M, Klenk HD, Garten W. Identification and characterization of spodoptera frugiperda furin: a thermostable subtilisin-like endopeptidase. Biol Chem. Dec. 1998;379(12):1433-40.B23-B23.
Jarvis DL, Finn EE. Biochemical analysis of the N-glycosylation pathway in baculovirus-infected lepidopteran insect cells. Virology. Oct. 1, 1995;212(2):500-11.
Jarvis, DL et al, Developing baculovirus-insect cell expression systems for humanized recombinant glycoprotein production, 75(13), 6223-6227, 200.
Ribeiro JP, Pau W, Pifferi C, Renaudet O, Varrot A, Mahal LK, Imberty A. Characterization of a high-affinity sialic acid-specific CBM40 from Clostridium perfringens and engineering of a divalent form. Biochem J. Jul. 15, 2016;473(14):2109-18.
Noad R.J. et al. Multigene expression of protein complexes by iterative modification of genomic Bacmid DNA, BMC Molecular Biology 2009, 10:87 doi:10.1186/1471-2199-10-87.
Kost, T.A. et al. Baculovirus as versatile vectors for protein expression in insect and mammalian cells, Nature Biotechnology vol. 23, No. 5, 567-575, 2005.
Cerutti M. et al. Lepidopteran cells, an alternative for the production of recombinant antibodies? mAbs 4:3 294-309, 2012.
Juliant S. et al. Engineering the Baculovirus Genome to Produce Galactosylated Antibodies in Lepidopteran Cells. Glycosylation Engineering of Biopharmaceuticals: Methods and Protocols, Methods in Molecular Biology, vol. 988,DOI 10.1007/978-1-62703-327-5_5.

* cited by examiner

Figure 1
Insect cell
1. Introduction of the bacterial Mini-F origin of replication and a cassette expressing the kanamycin resistance gene Kan$^R$ into the baculovirus genome
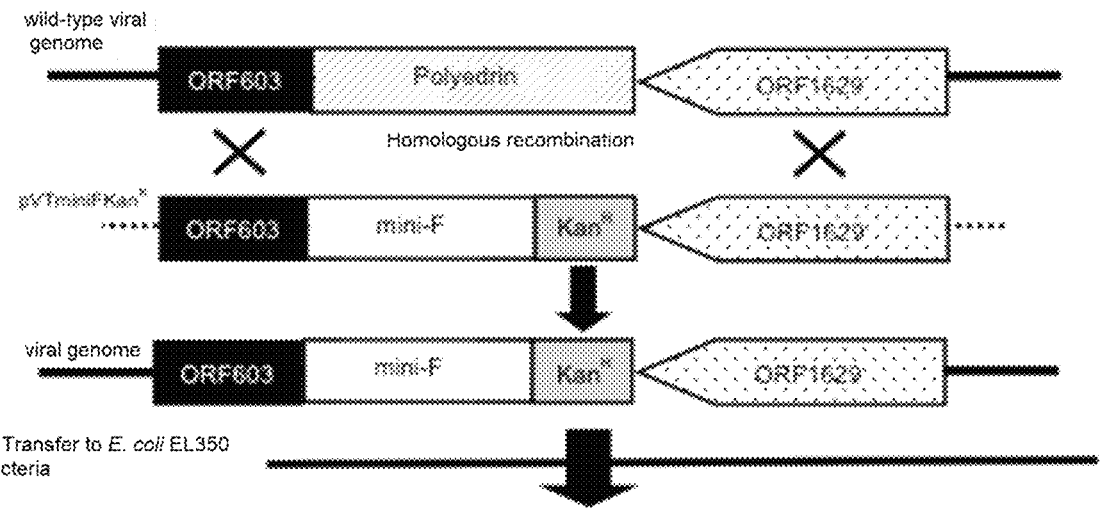
2. Transfer to *E. coli* EL350 bacteria
*E. coli* EL350 bacteria
3. Introduction of the ampicillin resistance gene
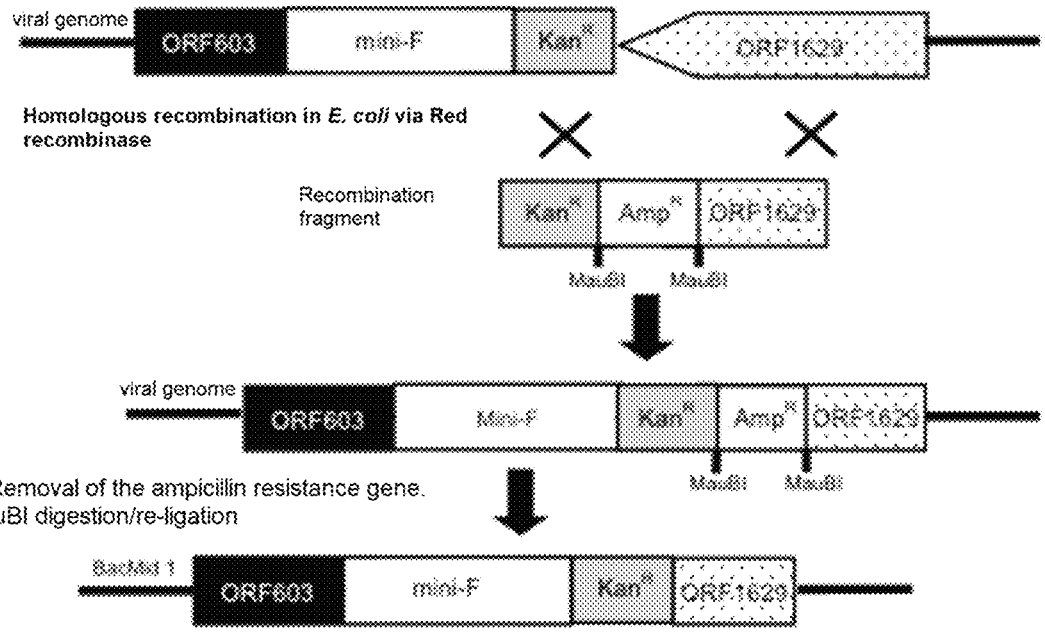
4. Removal of the ampicillin resistance gene. MauBI digestion/re-ligation
Production of BacMid 1

(*) Infectious viral DNA if the 2nd recombination in PH locus occurred.

1. Construction of a specific pVT/gp37 (pVT/gp37-Cγ1)

This vector contains the following expression cassette:

. Viral P10 promoter

. DNA sequence encoding a human immunoglobulin signal sequence (secretion sequence)

. 2 unique restriction sites for cloning of the variable region (VH) of the antibody (region that gives the specificity of the antibody)

. DNA sequence that encodes an epsilon, mu, alpha or gamma (γ1-4) human constant region.

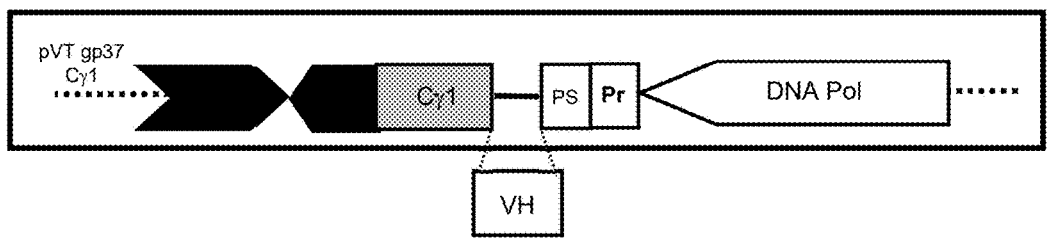

2. Insertion of the cDNA encoding the variable region of the antibody (VH).
This is thus reconstruction of the cDNA encoding the entire heavy chain.

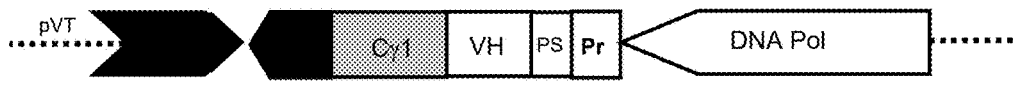

3. Generation of recombinant baculovirus.
Recombination between pVT/gp37 loaded with the heavy chain + pVT/PH loaded with the heavy chain + Bacmid 2.

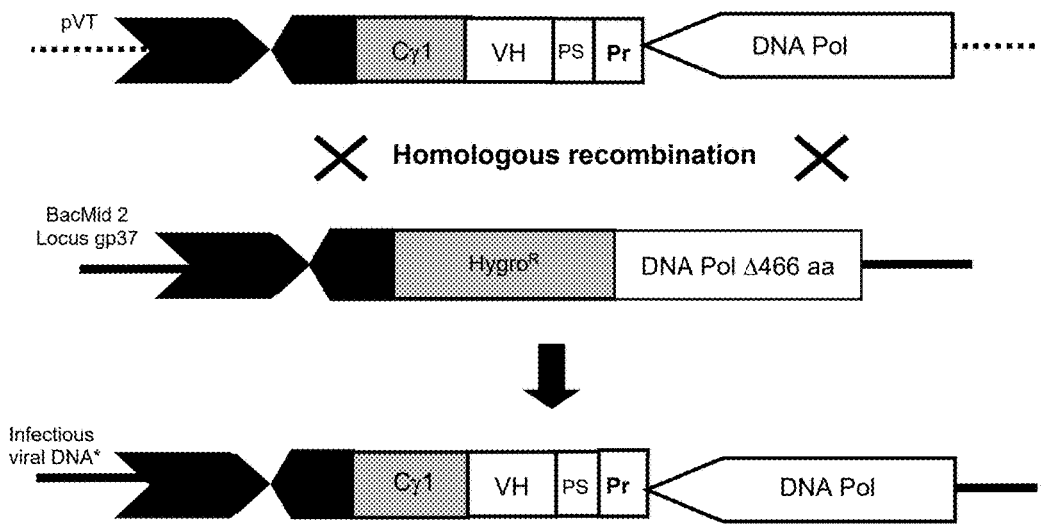

(*) Infectious viral DNA if recombination in the PH locus also occurred.

FIG. 6

(*) Infectious viral DNA if the 2nd recombination at the gp367 locus also occurred (*) Infectious viral DNA if the other 2 recombinations, at the PH and gp37 loci, also occurred.

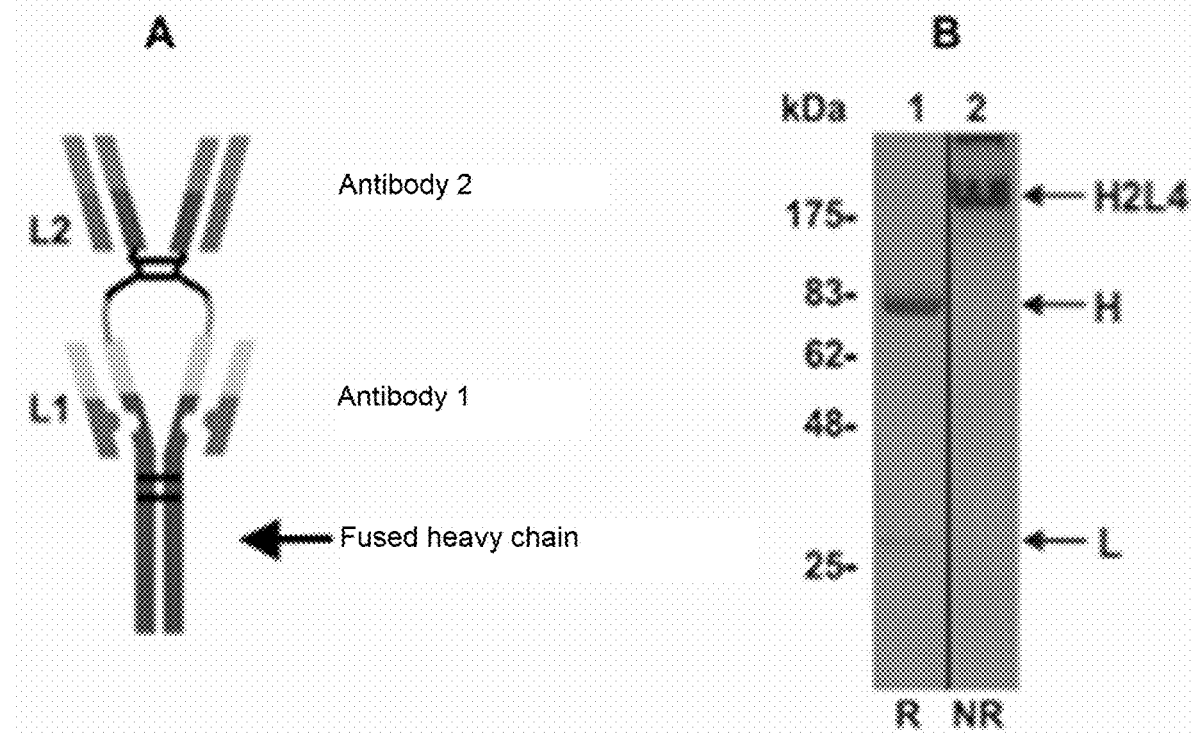

SEQUENCE LISTING

```
<160> NUMBER OF SEQ ID NOS: 3

<210> SEQ ID NO 1
<211> LENGTH: 75
<212> TYPE: DNA
<213> ORGANISM: Artificial Sequence
<220> FEATURE:
<223> OTHER INFORMATION: Synthetic wild-type P10 promoter
```

```
<400> SEQUENCE: 1
ataagaatta ttatcaaatc atttgtatat taattaaaat actatactgt aaattacatt        60
ttatttacaa tcatg                                                         75

<210> SEQ ID NO 2
<211> LENGTH: 71
<212> TYPE: DNA
<213> ORGANISM: Artificial Sequence
<220> FEATURE:
<223> OTHER INFORMATION: Synthetic P10S1A promoter

<400> SEQUENCE: 2
ataagtattt taatcttttc gtttgtataa attaatttat actatactgt ataaaaaaac        60
ctataaatat g                                                             71

<210> SEQ ID NO 3
<211> LENGTH: 71
<212> TYPE: DNA
<213> ORGANISM: Artificial Sequence
<220> FEATURE:
<223> OTHER INFORMATION: Synthetic P10S1B promoter

<400> SEQUENCE: 3
ataagtattt taatcttttc gtttgtacca ctgcagtggt actatactgt ataaaaaaac        60
ctataaatat g                                                             71
```

BACULOVIRUS EXPRESSION SYSTEM

TECHNICAL FIELD

The invention concerns a process for the preparation of a recombinant baculovirus comprising at least two exogenous genes, homologous recombination sets used in this preparation process, the recombinant baculoviruses obtained by this process, and the use of the recombinant baculoviruses for the production of polypeptides.

TECHNOLOGICAL BACKGROUND

Baculoviruses are a family of rod-shaped viruses, specific to arthropods, composed of four genera (Alphabaculovirus, Betabaculovirus, Deltabaculovirus, Gammabaculovirus) comprising 49 species. Baculoviruses are unable to replicate in mammalian or other vertebrate cells.

The baculovirus genome consists of a circular, double stranded DNA molecule of between 80 and 180 kbp in size. The baculovirus genome is associated with highly basic proteins of 6.5 kDa within a helically symmetrical nucleocapsid which contains a 39 kDa capsid protein. The size of the genome determines the length of the nucleocapsid. The nucleocapsid is further packaged within a lipoprotein envelope to form the virus particle or virion. These structures may be occluded within a crystalline matrix or polyhedron consisting largely of a single protein (polyhedrin) of about 30 kDa. Polyhedra are large structures ranging in size from 1 to 15 μm in diameter with an outer polysaccharide envelope which confers additional protection.

Baculoviruses with a genetically modified genome are used in biotechnology for the production of recombinant proteins (i.e. recombinant baculoviruses). After entering an insect cell, these recombinant baculoviruses will use the insect cell's machinery to produce the recombinant protein.

Recombinant baculoviruses are obtained by inserting one or more genes from other species (e.g. humans, other vertebrates, plants, bacteria and viruses) into the genome of a parental baculovirus. These genes are placed under the control of a viral or cellular promoter (e.g. the polyhedrin gene promoter) to generate a recombinant baculovirus. The promoter allows transcription of the foreign gene into messenger RNA which, in turn, is translated into protein in the recombinant baculovirus-infected insect cell. The advantage of using this system is that the level of recombinant protein production in recombinant baculovirus-infected insect cells can be very high. The recombinant protein can then be purified from the infected cells if the protein is intracellular or from the culture medium if the protein is secreted. The baculovirus expression system is widely used in industry and in research laboratories. In addition to the high productivity of the baculovirus expression system, this system is also highly valued because it allows the production of biologically active recombinant proteins. Indeed, insect cells generally allow suitable post-translational modifications to be obtained.

Despite all these advantages, the baculovirus expression system is difficult to implement on an industrial scale for the production of several distinct recombinant polypeptide sequences, for example proteins comprising several distinct subunits, such as antibodies or pairs of viral proteins. Indeed, the processes used for the production of recombinant baculoviruses are complex and require a large number of steps that do not allow homogeneous and stable recombinant baculovirus genomes to be obtained. The homogeneity and stability of recombinant baculovirus genomes are necessary criteria in order to envisage industrial development.

There is therefore a need to develop processes that are easy to implement, that allow the production of recombinant proteins comprising several distinct subunits, such as antibodies, in baculovirus expression systems, and that can be developed on an industrial scale in particular.

On the basis of the above, the applicant has developed a process for preparing homogeneous and stable recombinant baculoviruses which is particularly efficient and easy to implement, and which makes it possible to envisage industrial development, notably for the production of several distinct recombinant polypeptide sequences, particularly proteins comprising several distinct subunits.

SUMMARY OF THE INVENTION

In a first aspect, the invention concerns a process for preparing, in an insect cell, a recombinant baculovirus comprising n exogenous genes, by recombination between:
a) a replication-deficient baculovirus genome in which n genes essential for viral replication are non-functional; and
b) n transfer vectors each comprising:
  i) a nucleotide sequence that restores the function of one of the n non-functional genes essential for viral replication,
  ii) one of the n exogenous genes,
the set of nucleotide sequences i) of the n vectors being able to restore replication of the replication-deficient baculovirus genome;
n being an integer at least equal to 2.

In a second aspect, the invention concerns a recombinant baculovirus comprising (i.e. "recombinant baculovirus whose genome comprises" or "recombinant baculovirus whose genome encodes") n nucleotide sequences of formula (I):

[exogenous gene]-[spacer nucleotide sequence]-
[functional gene essential for viral replication]    (I), said spacer nucleic acid sequence consists of 0 (zero) to 600 bp, said functional gene essential for viral replication is selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6); n being an integer at least equal to 2.

In a third aspect, the invention concerns a set of homologous recombination elements comprising:
a) a replication-deficient baculovirus genome in which n genes essential for viral replication are non-functional;
b) n transfer vectors each comprising:
  i) a nucleic acid sequence that restores the function of one of the n non-functional genes essential for viral replication,
  ii) optionally an exogenous gene,
n being an integer at least equal to 2.

In a fourth aspect, the invention concerns a cell comprising a recombinant baculovirus of the invention or a set of homologous recombination elements of the invention.

In a fifth aspect, the invention concerns the use of a recombinant baculovirus of the invention or a cell of the invention for the production of n exogenous polypeptides encoded by n exogenous genes.

DETAILED DESCRIPTION OF THE INVENTION

Preparation of the Recombinant Baculovirus

The invention concerns a process for preparing, in an insect cell, a recombinant baculovirus comprising n exogenous genes, by recombination between:
- a) a replication-deficient baculovirus genome in which n genes essential for viral replication are non-functional; and
- b) n transfer vectors each comprising:
  - i) a nucleotide sequence that restores the function of one of the n non-functional genes essential for viral replication,
  - ii) one of the n exogenous genes, the set of nucleotide sequences i) of the n vectors being able to restore replication of the replication-deficient baculovirus genome;
- n being an integer at least equal to 2.

In the context of the present invention, the expression "baculovirus genome" refers to all the genetic material of a baculovirus, including in particular all the coding sequences and non-coding DNA of a baculovirus.

In the context of the present invention, the term "replication-deficient baculovirus genome" means a baculovirus genome in which n genes essential for viral replication have been either deleted (fully or partially) or mutated in such a way that the baculovirus genome has lost its ability to replicate in an insect cell. For example, the gene essential for viral replication is no longer expressed or is transcribed and then translated into a non-functional protein. Thus, deleted (fully or partially) or mutated genes are called "non-functional genes essential for viral replication". Viral replication-deficient baculovirus genomes are produced from parental baculovirus genomes using molecular biology techniques well known to the skilled person, and in particular those allowing nucleotide sequences to be inserted into and/or deleted from the parental baculovirus. Preferably, the viral replication-deficient baculovirus genome comprises at least one nucleotide sequence allowing it to replicate within a bacterial cell. These nucleotide sequences are not exogenous genes in the sense of the invention. An example of a bacterial replication element is the "Mini-F" nucleotide sequence. Such replication elements are well known in the state of the art. The bacterial cell can be *Escherichia coli*. A baculovirus genome that comprises a nucleotide sequence allowing it to replicate within a bacterial cell is known as a "BacMid". Preferably, the replication-deficient baculovirus genome also comprises one or more nucleotide sequences encoding one or more selectable markers for selecting or identifying bacterial cells transfected with the replication-deficient baculovirus genome. These nucleotide sequences are not exogenous genes in the sense of the invention. Examples of selectable markers are the ampicillin resistance gene, the kanamycin resistance gene, the hygromycin resistance gene, the zeocin resistance gene and/or the tetracycline resistance gene.

In a particular embodiment, the replication-deficient baculovirus genome is obtained from a baculovirus genome selected among or derived from the genome of BmNPV, AcMNPV, ApNPV, BsSNPV, CfMNPV, EOSNPV, HaNPV, HzNPV, LdMNPV, MbMNPV, OpMNPV, SlMNPV, SeMNPV or TeNPV, preferably AcMNPV.

In a preferred embodiment, the replication-deficient baculovirus genome is circular. The process according to the invention does not require linearization of the replication-deficient genome.

In the context of the present invention, the expression "recombinant baculovirus genome" refers to the baculovirus genome resulting from homologous recombination between the viral replication-deficient baculovirus genome and the n transfer vectors.

In the context of the present invention, the expression "recombinant baculovirus" refers to a baculovirus whose genome is a recombinant baculovirus genome, i.e. a baculovirus encoding the n exogenous genes. The recombinant baculovirus is produced after replication of the recombinant baculovirus genome in the insect cell. The recombinant baculovirus can be secreted and can infect another insect cell. Preferably, the recombinant baculovirus of the invention is infectious. "Gene" means a nucleotide sequence that can be transcribed into a protein or peptide of interest.

In the context of the present invention, "exogenous gene" (or "transgene") means a gene that is not naturally present in the baculovirus genome. Examples include human genes, animal genes, viral genes or bacterial genes. In addition, an "exogenous gene" in the sense of the invention is not present in the viral replication-deficient baculovirus genome. Thus, genes that are not naturally present in the baculovirus genome but are present in the viral replication-deficient baculovirus genome are not considered exogenous genes in the sense of the present invention. In other words, exogenous genes are carried by transfer vectors which recombine with the viral replication-deficient baculovirus genome and are then integrated into the recombinant baculovirus.

An exogenous gene in the sense of the present invention is placed under the control of suitable elements for its expression in the insect cell. "Suitable elements" means all the elements necessary for its transcription into messenger RNA (mRNA) and for translation of the mRNA into protein. Among the elements necessary for transcription, the promoter takes on particular importance. It may be a constituent promoter or a regulated promoter, and it may be of baculoviral origin or arthropod origin (e.g. insect origin). What is important is that the chosen promoter is suitable for expression of the exogenous gene in the insect cell. In general, a promoter in use in the present invention may be modified so as to contain regulatory sequences. Examples of promoters include the polyhedrin promoter, the P10 promoter, synthetic promoters derived from the polyhedrin and P10 promoters, the baculovirus CfMNPV IE1 promoter, the baculovirus LdMNPV IE1 promoter, the baculovirus OpMNPV gp64 promoter, the shrimp white spot syndrome virus (WSSV) IE1 promoter, the *Junonia coenia* densovirus (JcDNV) P9 promoter, the silkworm *Bombyx mori* actin 3 (A3) cellular promoter. In a particular embodiment, one or more of the exogenous genes is placed under the control of a synthetic promoter derived from the wild-type P10 promoter (SEQ ID NO: 1), preferably the synthetic promoter P10S1A (SEQ ID NO: 2) or P10S1B (SEQ ID NO: 3).

"Expression cassette" means a nucleotide sequence generally consisting of one or more genes and elements suitable for its/their expression, for example an exogenous gene and the elements suitable for its expression in the insect cell.

In the context of the invention, the recombinant baculovirus expresses (i.e. produces) the n exogenous genes in an insect cell. In a particular embodiment, the insect cell is selected from Sf9, Sf21, Tn5-b14, baculovirus AcMNPV-sensitive lepidopteran cell lines or Sf21 cell lines, preferably Sf9.

The transfer vectors may also contain one or more nucleotide sequences allowing them to replicate within a bacterial cell. They may also contain genes encoding a selectable marker for selecting or identifying bacterial cells transformed with a transfer vector.

One of the main advantages of the present invention is that the ability of the viral replication-deficient baculovirus genome to replicate is restored by recombination with the n transfer vectors. Indeed, each of the n transfer vectors encodes, in addition to one of the n exogenous genes, a nucleotide sequence that restores the function of one of the n non-functional genes essential for viral replication. Thus, only recombination with the n transfer vectors is able to restore replication of the replication-deficient baculovirus genome. Thus, the process of the invention guarantees that only the recombinant baculovirus genomes containing the n exogenous genes can generate infectious recombinant baculoviruses. This process avoids the need to use time-consuming tests to identify the recombinant baculoviruses containing the n exogenous genes.

In a preferred embodiment, the genes essential for viral replication are selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6). These genes are preferred because they are adjacent to a gene non-essential for viral replication. Thus, in a preferred embodiment, in the viral replication-deficient baculovirus genome, the n non-functional genes essential for viral replication are each adjacent to a gene non-essential for viral replication. As detailed throughout the present application, the n exogenous genes each recombine at the level of a gene non-essential for viral replication adjacent to a non-functional gene essential for viral replication. Given that the gene non-essential for viral replication is non-essential for replication of the baculovirus genome, this recombination does not affect the ability of the baculovirus genome to replicate.

In the sense of the present invention, the expression "replication" or "viral replication" means replication of both the baculovirus genome and the baculovirus. It should be understood that replication of the baculovirus genome in an insect cell is essential for replication of the baculovirus in the insect cell. Thus, a gene essential for viral replication is understood to be a gene essential for replication of the baculovirus. Replication of the baculovirus in the insect cell generates infectious baculoviruses. Thus, the process of the invention generates an infectious recombinant baculovirus in the insect cell.

In the sense of the present invention, a non-functional gene essential for viral replication is adjacent to a gene non-essential for viral replication when the two genes follow or partially overlap each other on the baculovirus genome; preferably no other gene is between the non-functional gene essential for viral replication and the gene non-essential for viral replication. Advantageously, the two genes mentioned above are separated by a spacer nucleotide sequence, for example a non-coding spacer nucleotide sequence. In particular, the spacer nucleotide sequence has a length ranging from 1 bp to 600 bp. It is also possible that no spacer nucleotide sequence (i.e. 0 bp) separates the two genes mentioned above, i.e. the two genes mentioned above are side by side on the baculovirus genome or partially overlap. Alternatively, the spacer nucleotide sequence may comprise a gene non-essential for viral replication.

The applicant also noticed that the choice of non-functional genes essential for viral replication adjacent to genes non-essential for viral replication was particularly advantageous and made it possible to obtain homogeneous homologous recombinations and thus to prepare recombinant baculoviruses whose genomes are homogeneous. As explained above, only perfect recombination of the n vectors produces a recombinant baculovirus able to replicate in an insect cell. For the purposes of the present invention, it is preferable that the genomes of the recombinant baculoviruses prepared according to the invention be more than 90% homogeneous, advantageously more than 95% homogeneous, preferably more than 99% homogeneous and most preferably around 100% homogeneous, preferably identical.

In a particular embodiment, the gene non-essential for viral replication is selected from Ph (ORF 8), ORF11, ORF13, egt (ORF15), u-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif4 (ORF96) he65 (ORF105), ORF108, ORF110, cathepsin (ORF127), p24 (ORF129), pp34 (ORF131), ORF134, ORF145, odv-e56 (ORF148), ORF5.

Advantageously, the gene pair essential for viral replication/non-essential for viral replication is selected from the pairs listed in the following table:

| Pair | Essential gene | Non-essential gene | Spacing between the 2 genes |
|---|---|---|---|
| 1 | 1629 (ORF9) | Ph (ORF 8) | 29 bp |
| 2 | Pk1 (ORF10) | ORF11 | 163 bp |
| 3 | lef-1 (ORF14) | ORF13 | Overlap |
|   |   | or egt (ORF15) | 112 bp |
| 4 | ORF34 | v-ubiquitin (ORF35) | 20 bp |
| 5 | lef-11 (ORF37) | 39K (ORF36) | Overlap |
|   |   | or ORF38 | Overlap |
| 6 | p47 (ORF40) | p43 (ORF39) | 7 bp |
|   |   | or lef-12 (ORF41) | Overlap |
| 7 | Lef8 (ORF50) | pcna (ORF49) | 109 bp |
| 8 | DNAJ domain (ORF51) | ORF52 | 202 bp |
| 9 | ORF53 | ORF52 | 1 bp |
| 10 | vp1054 (ORF54) | ORF55 | 91 bp |
| 11 | Lef-9 (ORF62) | Fp (ORF61) | 26 bp |
|   |   | or ORF63 | 60 bp |
| 12 | DNA Pol (ORF65) | gp37(ORF64) | 137 bp |
| 13 | lef-3 (ORF67) | ORF68 | Overlap |
| 14 | ORF73 | ORF72 | 8 bp |
| 15 | ORF75 | ORF74 | 17 bp |
| 16 | ORF81 | ORF82 | Overlap |
| 17 | p95 (ORF83) | ORF82 | Overlap |
| 18 | vp39 (ORF89) | cg30 (ORF88) | 2 bp |
| 19 | lef-4 (ORF90) | ORF91 | 0 bp |
| 20 | p33 (ORF92) | ORF91 | 37 bp |
| 21 | helicase (ORF95) | pif-4 (ORF96) | Overlap |
| 22 | vp80 (ORF104) | he65 (ORF105) | 27 bp |
| 23 | ORF106-107 | he65 (ORF105) | 544 bp |
| 24 | odv-ec43 (ORF109) | ORF108 | 11 bp |
|   |   | or ORF110 | 35 bp |
| 25 | gp64/67 (ORF128) | cathepsin (ORF127) | 224 bp |
|   |   | or p24 (ORF129) | 182 bp |
| 26 | ORF132 | pp34 (ORF131) | 211 bp |
| 27 | ORF133 | ORF134 | 50 bp |

| Pair | Essential gene | Non-essential gene | Spacing between the 2 genes |
|---|---|---|---|
| 28 | odv-ec27 (ORF144) | ORF145 | 69 bp |
| 29 | ORF146 | ORF145 | Overlap |
| 30 | ie1 (ORF147) | odv-e56 (ORF148) | 61 bp |
| 31 | lef-2 (ORF6) | ORF5 | Overlap |

In the context of the present invention, the expression "homologous recombination" refers to the exchange of genetic information between two different nucleotide sequences, requiring the presence of homologous sequences between the two different nucleotide sequences. In the context of the present invention, recombination takes place in the insect cell between (a) a replication-deficient baculovirus genome in which n genes essential for viral replication are non-functional and (b) the n transfer vectors. Recombination in the context of the present invention takes place in a single step in the insect cell. In other words, recombination of the n exogenous genes with the replication-deficient baculovirus genome takes place simultaneously or almost simultaneously in the insect cell.

The process according to the invention uses an intermolecular homologous recombination mechanism. In general, the homologous recombination mechanism consists of the exchange of homologous nucleotide sequences between the replication-deficient baculovirus genome and the n transfer vectors. These nucleotide sequences may be identical or substantially homologous. In a particularly advantageous embodiment, the transfer vectors comprise, on either side of the exogenous gene expression cassette, flanking sequences homologous to the replication-deficient baculovirus genome. The degree of homology of the flanking sequences to the corresponding part of the replication-deficient baculovirus genome may be variable but must be sufficient to allow intermolecular recombination. For the purposes of the present invention, it is preferable that it be greater than 70%, advantageously greater than 80%, preferably greater than 90% and most preferably around 100%, preferably identical. Furthermore, a short region of homology may be sufficient, i.e. at least 10 consecutive nucleotides (or base pairs) common between the flanking sequences and their homologous sequences in the replication-deficient baculovirus genome. In the context of the present invention, the length of the flanking sequences may range from 10 bp (i.e. 10 base pairs) to 10 kb (i.e. 10 000 base pairs), advantageously from 100 bp to 6 kb, preferably from 200 bp to 6 kb and, most preferably, from 400 bp to 6 kb. Thus, the genetic material located between the flanking sequences of the n transfer vectors replaces the genetic material located between the two sequences homologous to the flanking sequences of the replication-deficient baculovirus genome. This intermolecular exchange generates an infectious recombinant baculovirus in the insect cell. According to the invention, the set of nucleotide sequences i) (i.e. the nucleotide sequences that restore the function of the n non-functional genes essential for viral replication) of the n transfer vectors are able to restore replication of the replication-deficient baculovirus genome. Indeed, intermolecular exchange restores the function of the n non-functional genes essential for viral replication. In other words, restoration of the function of the n non-functional genes essential for viral replication takes place when homologous recombination occurs correctly. This is because the n transfer vectors each comprise a nucleotide sequence that restores the function of one of the n non-functional genes essential for viral replication.

For example, when n=2, a replication-deficient baculovirus genome in which two genes essential for viral replication are non-functional recombines with two transfer vectors that each comprise a nucleotide sequence that restores the function of one of the two non-functional genes essential for viral replication. This means that recombination with the first transfer vector restores the function of a first non-functional gene essential for viral replication and recombination with the second transfer vector restores the function of a second non-functional gene essential for viral replication. Therefore, only recombination of the two transfer vectors with the replication-deficient baculovirus genome restores the function of the two non-functional genes essential for viral replication and thus restores replication of the replication-deficient baculovirus genome. This restoration generates infectious recombinant baculoviruses in the insect cell.

Thus, according to the process of the invention, recombination with the n transfer vectors, or multi-recombination, is necessary to restore replication of the replication-deficient baculovirus genome.

Surprisingly, the inventors have demonstrated that multi-recombination could be done in a single step in the insect cell. This is particularly advantageous since the replication-deficient baculovirus genome and the n transfer vectors can be introduced at the same time into the insect cell, meaning that the replication-deficient baculovirus genome and the transfer vectors are introduced simultaneously into the insect cell, in other words the replication-deficient baculovirus genome and the transfer vectors are introduced in a single step into the insect cell. Multi-recombination in a single step during the process according to the invention is therefore very easy to implement and produces homogeneous recombinant baculovirus genomes, meaning that the homology of the nucleotide sequence of each recombinant baculovirus genome produced is greater than 90%, preferably greater than 95%, preferably greater than 99%, preferably around 100%, preferably equal to 100%.

The process according to the invention makes it possible to prepare a recombinant baculovirus expressing (i.e. producing) n exogenous polypeptides. The n exogenous polypeptides form a single protein or several proteins. "Polypeptide" means a chain of amino acids linked by peptide bonds. For example, a polypeptide may be a protein, a protein subunit, a protein fragment or simply an amino acid chain. Generally, a polypeptide is made up of at least 10 amino acids.

In a particular embodiment, the n exogenous polypeptides form several proteins. They may be proteins comprising a single polypeptide chain, several identical subunits or several distinct subunits. The number of proteins produced may be equal to or less than n. For example, three exogenous polypeptides (n=3) may form (i) a protein comprising a single polypeptide chain and a protein comprising two distinct subunits, (ii) three proteins comprising a single polypeptide chain, (iii) a protein comprising several identical subunits and a protein comprising two distinct subunits or (iv) three proteins comprising several identical subunits.

In another particular embodiment, the n exogenous polypeptides form a single protein. In this embodiment, the protein generally comprises n distinct subunits.

The process according to the invention is particularly advantageous for preparing a recombinant baculovirus expressing (i.e. producing) an exogenous protein comprising several distinct subunits, for example a protein having its function only when it comprises all its subunits. The subunits are generally linked together by non-covalent bonds (e.g. hydrophobic bonds) and/or covalent bonds (e.g. disulphide bridges between two cysteines).

In a particular embodiment, the process according to the invention makes it possible to easily and quickly prepare a recombinant baculovirus comprising n distinct exogenous genes that encode a single protein comprising n distinct subunits. "Distinct exogenous genes" means genes not having the same nucleotide sequence. "Distinct subunits" means peptide sequences not having the same amino acid sequence. Thus, a "protein comprising n distinct subunits" comprises n distinct subunits linked together by non-covalent bonds and/or covalent bonds. In this embodiment, the number of transfer vectors will depend on the number of distinct subunits that the protein contains. For example, two transfer vectors will be used for a protein comprising two distinct subunits, three transfer vectors will be used for a protein comprising three distinct subunits, etc. Therefore, each transfer vector comprises an exogenous gene different from the exogenous genes comprised in the other transfer vectors. The recombinant baculovirus of the invention can comprise the entire protein of interest (i.e. all the distinct subunits that make up the protein of interest) only if recombination takes place between the replication-deficient baculovirus genome and the n transfer vectors.

According to the invention, n is an integer at least equal to 2, for example an integer ranging from 2 to 30, for example ranging from 2 to 10. For example, for a protein comprising several distinct subunits, the value of n will correspond to the number of distinct subunits that make up said protein.

In a particular embodiment, n=2 and the recombinant baculovirus encodes 2 exogenous genes that encode a protein comprising two subunits, advantageously 2 distinct exogenous genes that encode a protein comprising 2 distinct subunits. Preferably, the protein is an antibody, a protein complex forming virus-like particles (VLPs), a pair of viral proteins, a peptide hormone, preferably an antibody.

In a particular embodiment, n=3 and the recombinant baculovirus comprises 3 exogenous genes that encode a protein comprising three subunits, advantageously 3 distinct exogenous genes that encode a protein comprising 3 distinct subunits. Preferably, the protein is a bispecific antibody, a set of three viral proteins, a multienzyme complex, a protein complex, a protein complex forming VLPs, preferably a bispecific antibody.

The term "antibodies" is used herein in the broadest sense and encompasses various antibody structures widely described in the literature, including, but not limited to, antibodies of any origin, monoclonal antibodies, polyclonal antibodies and antibody fragments as long as they exhibit the desired activity (e.g. antigen binding). The antibody is an IgA, IgD, IgE, IgG or an IgM. Examples of antibody fragments include, but are not limited to, Fv, Fab, Fab', Fab'-SH, F(ab')2, Fc fragments; diabodies; scFv/Fc; camelid antibodies (e.g. VHHs); single-chain antibody molecules (e.g. scFv).

Advantageously, the recombinant baculovirus prepared according to the process of the invention does not comprise a nucleic acid sequence allowing it to replicate within a bacterial cell. In particular, the nucleic acid sequence allowing replication of the replication-deficient baculovirus genome within a bacterial cell is removed during homologous recombination in the insect cell.

The introduction into an insect cell of transfer vectors and of the replication-deficient baculovirus genome is carried out according to the general techniques widely described in the prior art. Particular mention may be made of the calcium phosphate technique, the DEAE-dextran technique, electroporation, methods based on osmotic shock, microinjection or methods based on the use of liposomes, preferably lipofection. In the context of the present invention, the transfer vectors and the replication-deficient baculovirus genome are introduced at the same time into the insect cell, meaning that the transfer vectors and the replication-deficient baculovirus genome are introduced simultaneously into the insect cell, in other words the transfer vectors and the replication-deficient baculovirus genome are introduced in a single step.

In the context of a process according to the invention, the quantities of replication-deficient baculovirus genome and of transfer vectors introduced into the insect cell may vary. It is preferred to use 5 times more of each of the transfer vectors than the quantity of replication-deficient baculovirus genome.

Another advantage of the present invention is that the replication-deficient baculovirus genome is introduced in circular form, i.e. with no prior linearization step. This linearization step is unnecessary since the baculovirus genome is replication-deficient, even in circular form, since it comprises non-functional genes essential for viral replication. The absence of a linearization step is another major advantage of the present invention.

Recombinant Baculovirus

The present invention also aims at protecting a recombinant baculovirus comprising (i.e. "recombinant baculovirus whose genome comprises" or "recombinant baculovirus whose genome encodes") n nucleotide sequences of formula (I):

[exogenous gene]-[spacer nucleotide sequence]-
[functional gene essential for viral replication]     (I), said spacer nucleic acid sequence consists of 0 (zero) to 600 bp, said functional gene essential for viral replication is selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6); n being an integer at least equal to 2.

Advantageously, the recombinant baculovirus according to the invention does not comprise a nucleic acid sequence allowing it to replicate within a bacterial cell. Indeed, it has been shown that the absence of such a sequence increases the stability of the recombinant baculovirus compared with a recombinant baculovirus having such a sequence (Piljmann et al. (2003) Journal of General Virology).

Advantageously, the recombinant baculovirus according to the invention does not comprise n genes non-essential for viral replication selected from Ph (ORF 8), ORF11, ORF13, egt (ORF15), v-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96) he65 (ORF105), ORF108, ORF110, cathepsin (ORF127), p24 (ORF129), pp34 (ORF131), ORF134, ORF145, odv-e56 (ORF148), ORF5. Advantageously, one of the n genes non-essential for viral replication is the gene encoding cathepsin because it has been shown that cathepsin can have a deleterious effect on the exogenous polypeptides produced.

According to the invention, n is an integer at least equal to 2, for example an integer ranging from 2 to 30, for example ranging from 2 to 10, as detailed in the section "Preparation of the recombinant baculovirus" above.

The present invention also aims at protecting a recombinant baculovirus, obtainable by the preparation process of the invention, comprising n nucleotide sequences of formula (I):

[exogenous gene]-[spacer nucleotide sequence]-
  [functional gene essential for viral replication]    (I), said spacer nucleic acid sequence consists of 0 (zero) to 600 bp, said functional gene essential for viral replication is selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6); n being an integer at least equal to 2.

Advantageously, the n nucleotide sequences are distributed throughout the recombinant baculovirus genome, thereby improving its stability. The selected n exogenous genes are therefore sufficiently spaced on the baculovirus genome. This feature is implicit since distribution on the genome is linked to the "essential gene/non-essential gene" pairs.

Advantageously, and this is inherent in the preparation process according to the invention, the n nucleotide sequences of formula (I) are not duplicated on the recombinant baculovirus genome. Indeed, it has been shown that the stability of the recombinant baculovirus decreases when the sequences are duplicated on the genome (data not presented).

Set of Homologous Recombination Elements

The present invention also aims at protecting a set of homologous recombination elements comprising:
  a) a replication-deficient baculovirus genome in which n genes essential for viral replication are non-functional;
  b) n transfer vectors each comprising:
    i) a nucleic acid sequence that restores the function of one of the n non-functional genes essential for viral replication,
    ii) optionally an exogenous gene,
  n being an integer at least equal to 2.

Advantageously, the non-functional genes essential for viral replication are each adjacent to a gene non-essential for viral replication, as described in the section "Preparation of the recombinant baculovirus" above.

In a particular embodiment, the transfer vectors comprise, on either side of the exogenous gene expression cassette, flanking sequences homologous to the replication-deficient baculovirus genome. Advantageously, the flanking sequences of each of the transfer vectors are homologous to all or part of said non-functional gene essential for viral replication and to all or part of said gene non-essential for viral replication. Advantageously, the flanking sequences have a length that can range from 10 bp (i.e. 10 base pairs) to 10 kb (i.e. 10 000 base pairs), advantageously from 100 bp to 6 kb, preferably from 200 bp to 6 kb and, most preferably, from 400 bp to 6 kb. The flanking sequences are described in detail in the section "Preparation of the recombinant baculovirus" above.

In a particular embodiment, the n transfer vectors each comprise an exogenous gene.

In a particular embodiment, the n exogenous genes encode n exogenous polypeptides. The n exogenous polypeptides form a single protein or several proteins, as detailed in the section "Preparation of the recombinant baculovirus" above.

In a particular embodiment, n=2 and the 2 exogenous genes encode a protein comprising two subunits, advantageously 2 distinct exogenous genes that encode a protein comprising 2 distinct subunits. Preferably, the protein is a monospecific antibody, a VLP, a pair of viral proteins, a peptide hormone, preferably an antibody.

In a particular embodiment, n=3 and the 3 exogenous genes encode a protein comprising three subunits, advantageously 3 distinct exogenous genes that encode a protein comprising 3 distinct subunits. Preferably, the protein is a bispecific antibody, a set of three viral proteins, a multienzyme complex, a protein complex, a VLP composed of 3 distinct proteins, preferably a bispecific antibody.

The "genes essential for viral replication" are described in the section "Preparation of the recombinant baculovirus" above.

In a particular embodiment, the replication-deficient baculovirus genome is obtained from a baculovirus genome selected among or derived from the genome of BmNPV, AcMNPV, ApNPV, BsSNPV, CMNPV, EOSNPV, HaNPV, HzNPV, LdMNPV, MbMNPV, OpMNPV, SlMNPV, SeMNPV or TeNPV, preferably AcMNPV.

The present invention also aims at protecting a cell comprising a recombinant baculovirus or a cell comprising a set of homologous recombination elements according to the invention.

In a particular embodiment, the cell is an insect cell, preferably selected from Sf9, Sf21, Tn5-b14, baculovirus AcMNPV-sensitive lepidopteran cell lines, Sf21 lines, preferably Sf9, as described in more detail in the section "Preparation of the recombinant baculovirus" above.

Process for the Production of Exogenous Polypeptides

The present invention also aims at protecting a process for the production of n exogenous polypeptides encoded by n exogenous genes comprising the steps of:
  a) Providing a replication-deficient baculovirus genome in which n genes essential for viral replication are non-functional;
  b) Providing n transfer vectors each comprising:
    i) a nucleotide sequence that restores the function of one of the n non-functional genes essential for viral replication,
    ii) one of the n exogenous genes encoding one of the n polypeptides, advantageously an expression cassette for one of the n exogenous genes encoding one of the n polypeptides,
    the set of nucleic acid sequences i) of the n vectors being able to restore replication of the replication-deficient baculovirus genome;
  c) Allowing the replication-deficient baculovirus genome and the n transfer vectors to recombine in an insect cell in order to generate an insect cell comprising a recombinant baculovirus genome able to replicate and able to generate recombinant baculoviruses comprising n exogenous genes; and d) Cultivating the insect cell under conditions suitable for producing the n exogenous polypeptides;

n being an integer at least equal to 2.

Unless otherwise specified, the definitions and embodiments described above, notably in the section "Preparation of the recombinant baculovirus", also apply to the section "Process for the production of exogenous polypeptides".

In a particular embodiment, the genes essential for viral replication are selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6), as detailed above in the section "Preparation of the recombinant baculovirus".

Advantageously, in said replication-deficient baculovirus genome, the n non-functional genes essential for viral replication are each adjacent to a gene non-essential for viral replication, as detailed in the section "Preparation of the recombinant baculovirus" above.

In a particular embodiment, the gene non-essential for viral replication is selected from those detailed above in the section "Preparation of the recombinant baculovirus".

Advantageously, the n exogenous genes each recombine at the level of a gene non-essential for viral replication adjacent to a non-functional gene essential for viral replication, as detailed in the section "Preparation of the recombinant baculovirus" above.

In a particular embodiment, the transfer vectors each comprise, on either side of the exogenous gene expression cassette, flanking sequences homologous to the replication-deficient baculovirus genome. Advantageously, the flanking sequences of each of the transfer vectors are homologous to all or part of said non-functional gene essential for viral replication and to all or part of said gene non-essential for viral replication. Advantageously, the flanking sequences have a length that can range from 10 bp (i.e. 10 base pairs) to 10 kb (i.e. 10 000 base pairs), advantageously from 100 bp to 6 kb, preferably from 200 bp to 6 kb and, most preferably, from 400 bp to 6 kb. The flanking sequences are described in detail in the section "Preparation of the recombinant baculovirus" above.

The n genes essential for viral replication are detailed in the section "Preparation of the recombinant baculovirus" above.

In a particular embodiment, the replication-deficient baculovirus genome is obtained from a baculovirus genome selected among or derived from the genome of baculovirus BmNPV, AcMNPV, ApNPV, BsSNPV, CfMNPV, EOSNPV, HaNPV, HzNPV, LdMNPV, MbMNPV, OpMNPV, SlMNPV, SeMNPV or TeNPV, preferably AcMNPV, as detailed in the section "Preparation of the recombinant baculovirus" above.

In a particular embodiment, the n exogenous polypeptides produced by the process according to the invention form several proteins. They may be proteins comprising a single polypeptide chain or several distinct subunits. The number of proteins produced may be equal to or less than n. For example, 3 exogenous polypeptides (n=3) may form (i) a protein comprising a single polypeptide chain and a protein comprising two subunits, or (ii) three proteins comprising a single polypeptide chain.

In another particular embodiment, the n exogenous polypeptides produced by the process according to the invention form a single protein. In this embodiment, the protein generally comprises n separate subunits.

In a particular embodiment the protein is a monoclonal antibody, a VLP composed of 3 distinct proteins, a pair of viral proteins, a peptide hormone, a bispecific antibody, a set of three viral proteins, a multienzyme complex, a protein complex.

In a particular embodiment, the insect cell is selected from Sf9, Sf21, Tn5-b14, baculovirus AcMNPV-sensitive lepidopteran cell lines, Sf21 lines, preferably Sf9, as detailed in the section "Preparation of the recombinant baculovirus" above.

In a particular embodiment, the replication-deficient baculovirus genome is obtained from a baculovirus genome selected among or derived from the genome of baculovirus BmNPV, AcMNPV, ApNPV, BsSNPV, CfMNPV, EOSNPV, HaNPV, HzNPV, LdMNPV, MbMNPV, OpMNPV, SlMNPV, SeMNPV or TeNPV, preferably AcMNPV, as detailed in the section "Preparation of the recombinant baculovirus" above.

In a particular embodiment, the replication-deficient baculovirus genome comprises at least one nucleotide sequence allowing it to replicate within a bacterial cell, as detailed in the section "Preparation of the recombinant baculovirus" above.

In a particular embodiment, the recombinant baculovirus capable of replication does not comprise a nucleotide sequence allowing it to replicate within a bacterial cell, as detailed in the section "Preparation of the recombinant baculovirus" above.

In the sense of the invention, "conditions suitable for producing the exogenous polypeptides" means the conditions under which the insect cells are cultivated to produce the exogenous polypeptides, notably a culture medium suitable for optimal cell growth, an optimal temperature and pH. The culture medium may contain serum of animal origin.

In a particular embodiment, the production process according to the invention further comprises a step b') to introduce the replication-deficient baculovirus genome and the n transfer vectors into an insect cell. As detailed above, introduction of the vectors into an insect cell is carried out according to the general techniques widely described in the prior art. Particular mention may be made of the calcium phosphate technique, the DEAE-dextran technique, electroporation, methods based on osmotic shock, microinjection or methods based on the use of liposomes, preferably lipofection. In the context of the present invention, the replication-deficient baculovirus genome and the transfer vectors are introduced at the same time into the insect cell, meaning simultaneously into the insect cell, in other words the replication-deficient baculovirus genome and the transfer vectors are introduced into the insect cell in a single step. Advantageously, the replication-deficient baculovirus genome is introduced into the insect cell in circular form, meaning that it is not linearized beforehand. As detailed above, introduction in circular form is another major advantage of the production process according to the invention.

The present invention also aims at the use of a recombinant baculovirus according to the invention or a cell according to the invention for the production of n exogenous polypeptides encoded by n exogenous genes.

FIGURES

FIG. 1 is a diagram illustrating the steps for the preparation of BacMid 1.

Legend:
  ORF: open reading frame
  Polyhedrin or PH: baculovirus gene encoding polyhedrin: gene non-essential for viral replication.
  ORF603: baculovirus gene encoding the 603 protein, non-essential gene.
  ORF1629: baculovirus gene encoding the 1629 protein: gene essential for viral replication PVT: transfer vector plasmid.
  Recombination fragment: DNA fragment containing the expression cassette to be integrated into the target DNA. This fragment has flanking regions on either side of the expression cassette to specifically target the region that will undergo homologous recombination in the bacterium via Red recombinase.
  Mini-F: bacterial origin of replication.
  KanR: bacterial expression cassette expressing the kanamycin resistance gene.
  AmpR: bacterial expression cassette expressing the ampicillin resistance gene.

FIG. 2 is a diagram illustrating the step of partial deletion of the gene encoding the viral DNA polymerase, the DNAPol gene, for the preparation of BacMid 2.

Legend:
  gp37: baculovirus gene encoding glycoprotein gp37, gene non-essential for viral replication.
  DNAPol: baculovirus gene encoding the viral DNA polymerase, gene essential for viral replication.
  DNAPol-Δ466 aa: DNAPol gene from which the region encoding the 466 C-terminal amino acids has been deleted
  Recombination fragment: DNA fragment containing the expression cassette to be integrated into the target DNA. This fragment has flanking regions on either side of the expression cassette to specifically target the region that will undergo homologous recombination in the bacterium via Red recombinase.
  HygroR: bacterial expression cassette expressing the hygromycin resistance gene.

Figure 3:
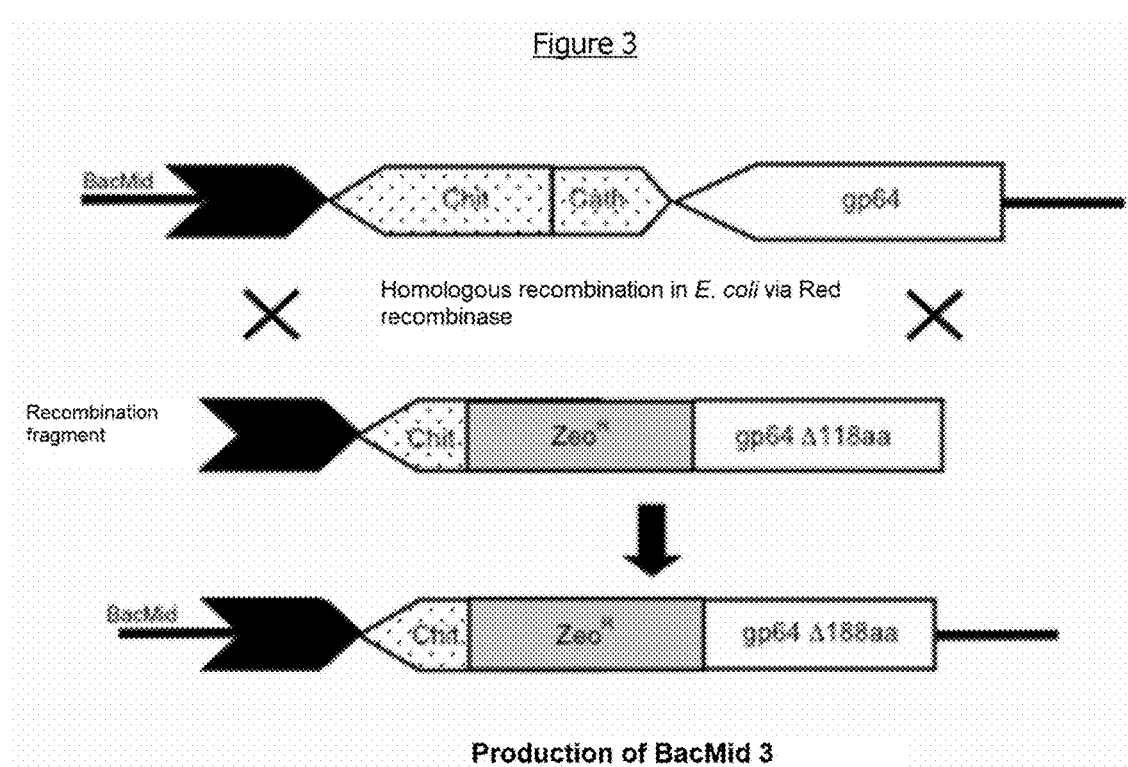

FIG. 3 is a diagram illustrating the step of partial deletion of the gene encoding gp64 for the preparation of BacMid 3.

Legend:
  Chit: baculovirus gene encoding chitinase, gene non-essential for viral replication.
  Cath: baculovirus gene encoding viral cathepsin, gene non-essential for viral replication.
  gp64: baculovirus gene encoding viral glycoprotein gp64, gene essential for viral replication.
  gp64-A188 aa: gp64 gene from which the region encoding the 188 C-terminal amino acids has been deleted.
  Recombination fragment: DNA fragment containing the expression cassette to be integrated into the target DNA. This fragment has flanking regions on either side of the expression cassette to specifically target the region that will undergo homologous recombination in the bacterium via Red recombinase.
  ZeoR: bacterial expression cassette expressing the zeocin resistance gene.

Figure 4:
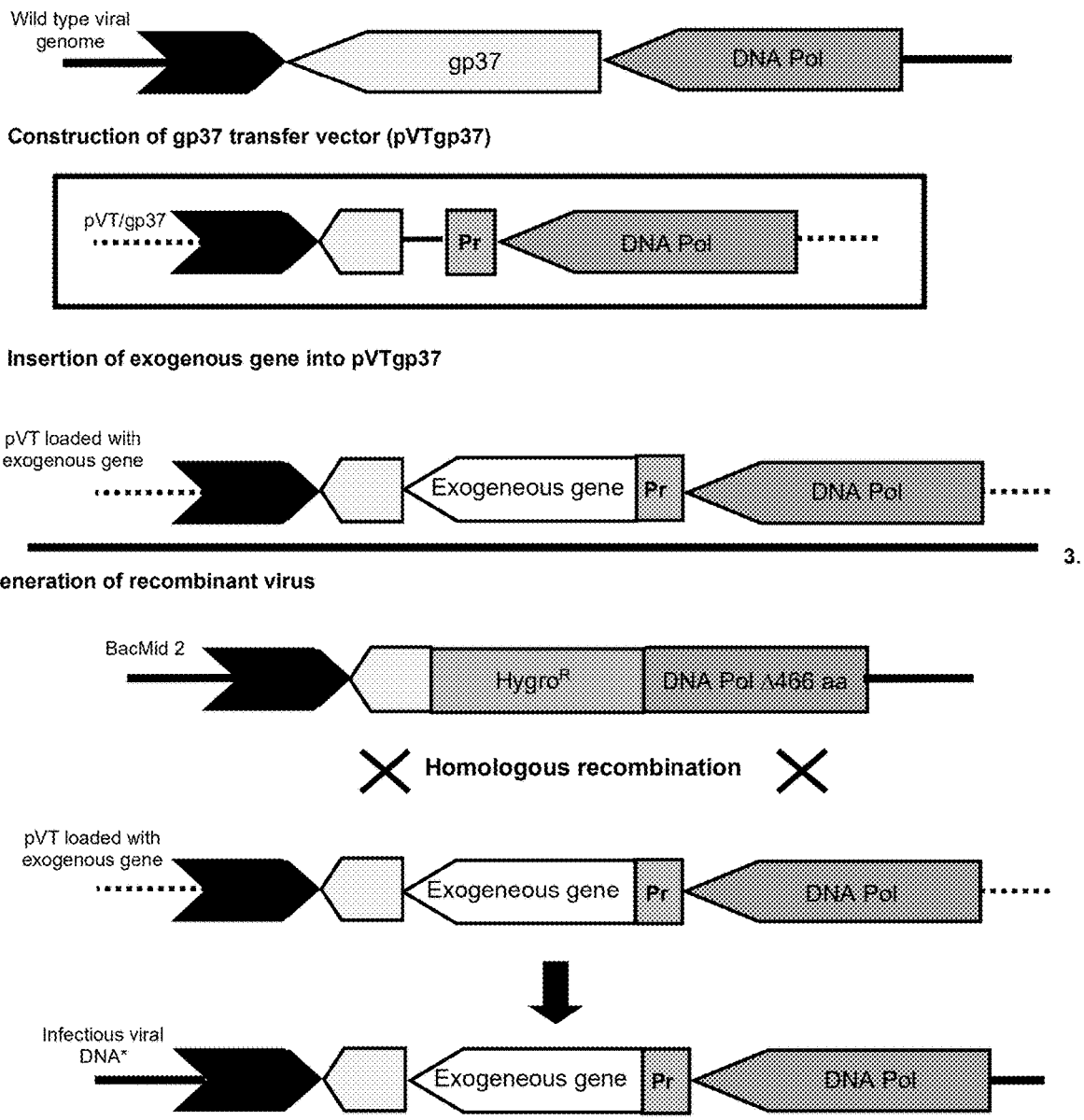

FIG. 4 is a diagram illustrating transfer vector pVT/gp37 and its use for the expression of a gene X (where X is a gene different from the gene encoding the heavy chain of an antibody).

Legend:
  PVT: transfer vector plasmid.
  gp37: baculovirus gene encoding glycoprotein gp37, gene non-essential for viral replication.
  DNAPol: baculovirus gene encoding the viral DNA polymerase, gene essential for viral replication.
  DNAPol-Δ466 aa: DNAPol gene from which the region encoding the 466 C-terminal amino acids has been deleted.
  Exogenous gene: gene of interest.
  Pr: viral or cellular promoter controlling expression of the exogenous gene.
  HygroR: bacterial expression cassette expressing the hygromycin resistance gene.

Figure 5:
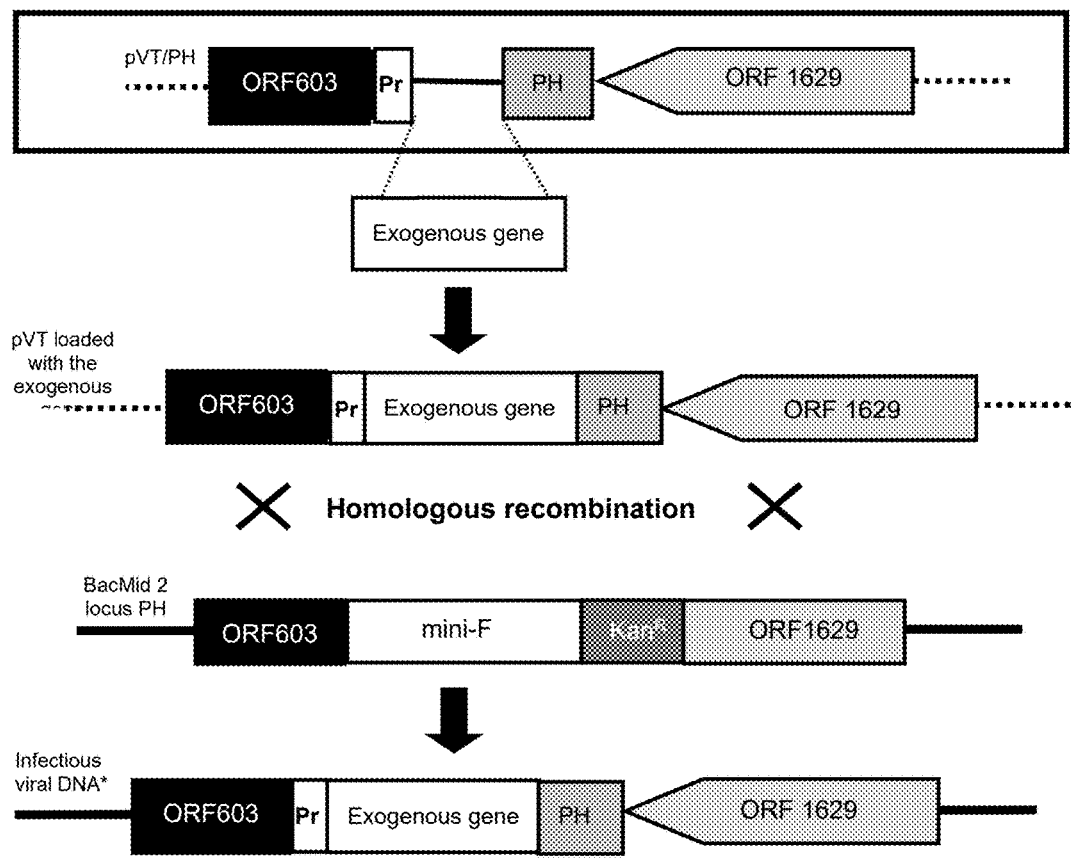

FIG. 5 is a diagram illustrating the construction and use of PH transfer vector pVT/PH for the expression of an exogenous gene X (where X is an exogenous gene different from the gene encoding a light chain of an antibody).

Legend:
  pVT/PH: polyhedrin transfer vector plasmid.
  PH: all or part of the baculovirus gene encoding polyhedrin, gene non-essential for viral replication.
  ORF603: baculovirus gene encoding the 603 protein.
  ORF1629: baculovirus gene encoding the 1629 protein, gene essential for viral replication.
  Exogenous gene: gene of interest.
  Pr: viral or cellular promoter controlling expression of the exogenous gene.
  KanR: bacterial expression cassette expressing the kanamycin resistance gene.
  Mini-F: bacterial origin of replication.

FIG. 6 is a diagram illustrating the construction and use of transfer vector pVT/gp37C■ for the expression of the heavy chain of an antibody.

Legend:
  pVT: transfer vector plasmid.
  PVT/gp37-Cy1: transfer vector plasmid specific for the heavy chain of an immunoglobulin, Cy1: cDNA encoding the γ1 constant domain of a human immunoglobulin.
  VH: cDNA encoding the variable domain of the heavy chain of an immunoglobulin.
  DNAPol: baculovirus gene encoding the viral DNA polymerase, gene essential for viral replication.
  DNAPolΔ466 aa: DNAPol gene from which the region encoding the 466 C-terminal amino acids has been deleted.
  Exogenous gene: gene of interest.
  Pr: viral or cellular promoter controlling expression of the exogenous gene.
  HygroR: bacterial expression cassette expressing the hygromycin resistance gene.
  PS: cDNA encoding a signal sequence (heavy chain secretion).

Figure 7:
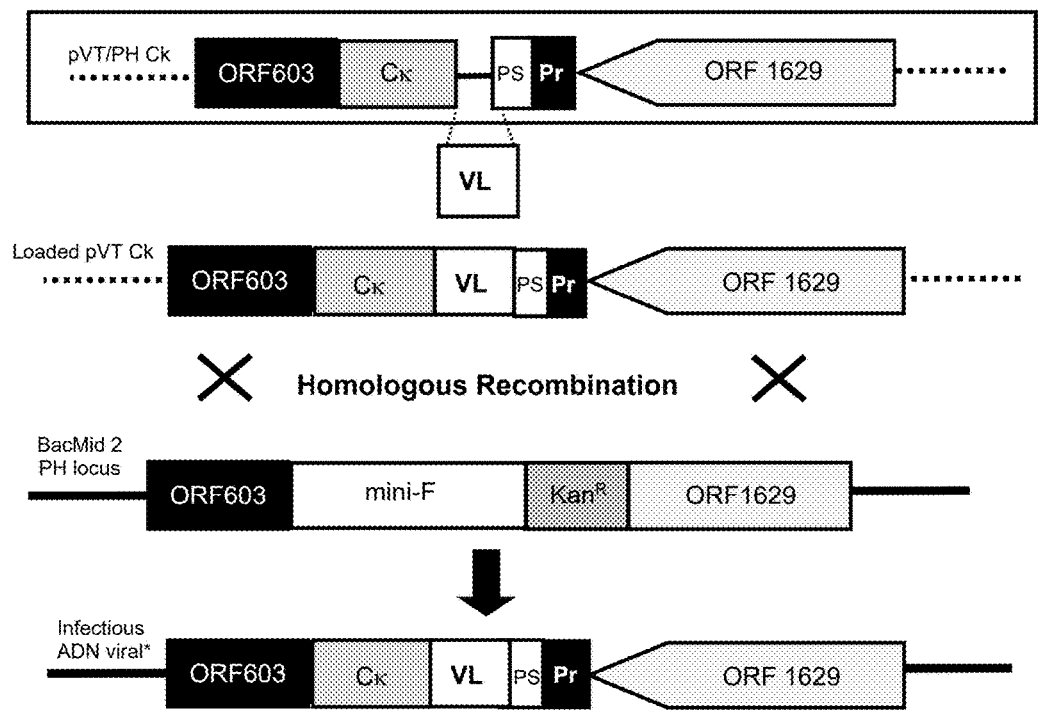

FIG. 7 is a diagram illustrating the construction and use of transfer vector pVT/PHCK for the expression of the light chain of an antibody.

Legend:
  ORF603: baculovirus gene encoding the 603 protein.
  ORF1629: baculovirus gene encoding the 1629 protein: gene essential for viral replication.
  Mini-F: bacterial origin of replication.
  pVT: transfer vector plasmid.
  PVT/PH-CK: transfer vector plasmid specific for the light chain of an immunoglobulin.
  CK: CDNA encoding the k constant domain of a human immunoglobulin.

VL: cDNA encoding the variable domain of the light chain of an immunoglobulin.

Pr: viral or cellular promoter controlling expression of the exogenous gene.

KanR: bacterial expression cassette expressing the kanamycin resistance gene.

PS: cDNA encoding a signal sequence (light chain secretion).

Figure 8:
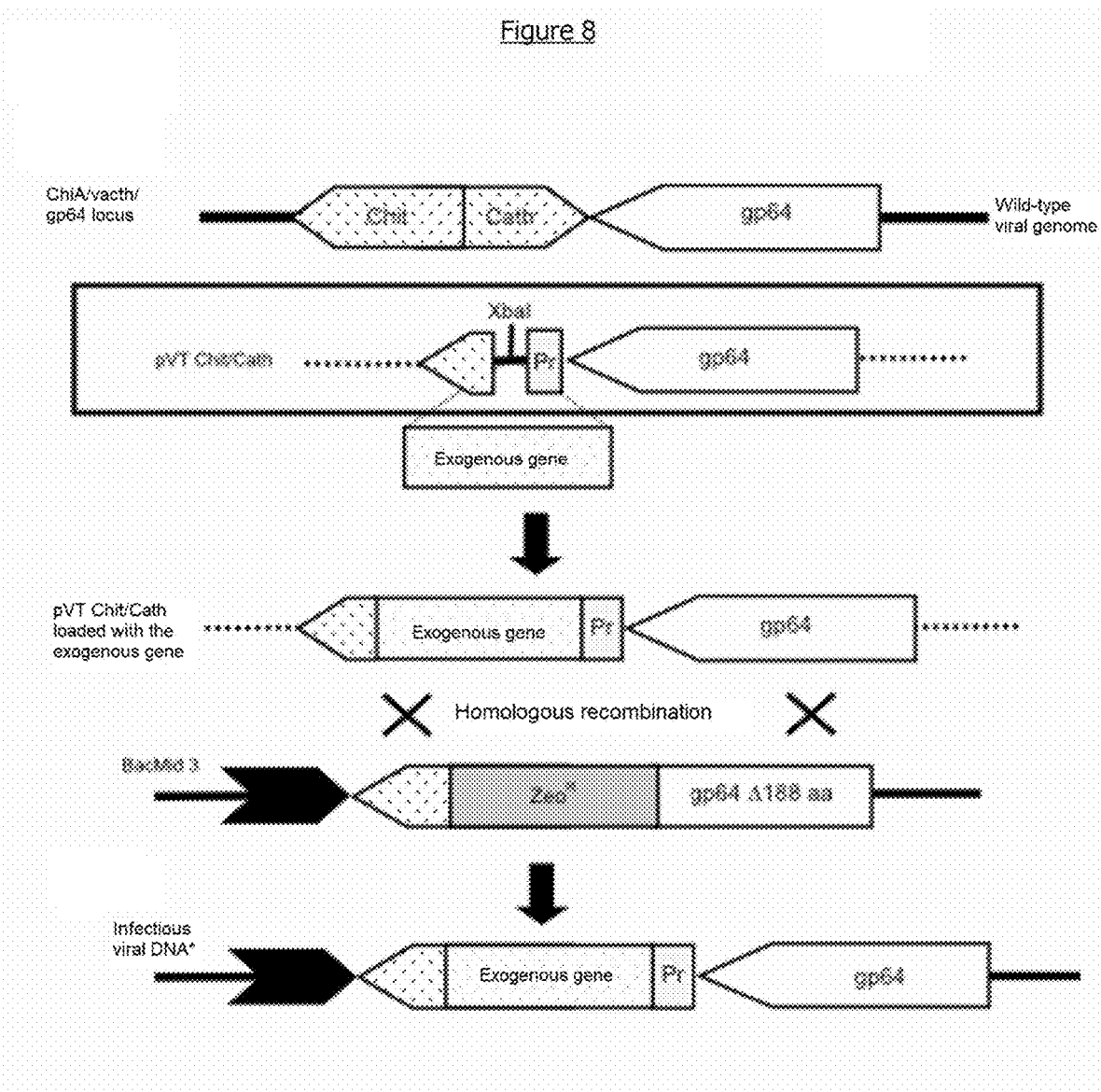

FIG. 8 is a diagram illustrating the construction of vector pVT/Chit-Cath and its use for the production of an exogenous gene.

Legend:
PVT: Transfer vector plasmid
pVT Chit/cath: Transfer vector plasmid specifically targeting the Chit/Cath region.
Chit: baculovirus gene encoding chitinase non-essential for viral replication
Cath: baculovirus gene encoding cathepsin non-essential for viral replication
Exogenous gene: gene of interest.
Pr: viral or cellular promoter controlling expression of the exogenous gene.
gp64: baculovirus gene encoding gp64, gene essential for viral replication
gp644188aa: gene encoding gp64 from which 566 bp have been deleted from the 3' end, leading to the production of a non-functional gp64 with a deletion of the 188 C-terminal amino acids.
ZeoR: bacterial expression cassette expressing the zeocin resistance gene.

Figure 9:
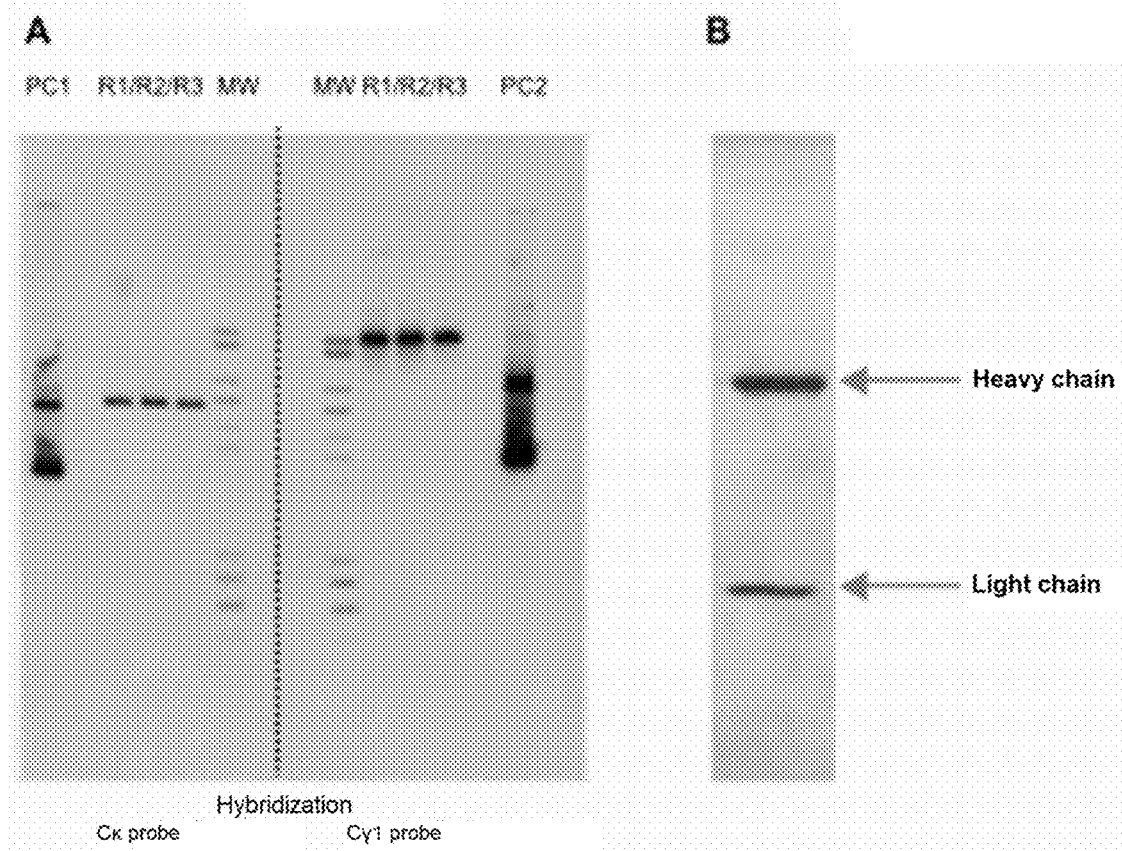

FIG. 9 is A) Southern blot analysis of the genome of 3 purified independent recombinant baculoviruses generated during the same transfection, and B) analysis of the recombinant antibody after purification on protein A.

Legend:
A: Analysis of the organization of the genomes of 3 independent recombinant baculoviruses expressing antibody 13B8II. These baculoviruses were isolated from a single transfection experiment. The hybridizations carried out respectively with a probe specific for the constant region of the kappa light chain: Ck probe, and a probe specific for the constant region of the gamma 1 heavy chain: Cγ1 probe, demonstrate correct and identical organization of the 3 recombinant viruses.
B. Analysis by polyacrylamide gel electrophoresis (SDS, 2-mercaptoethanol) and silver staining of the purified recombinant antibody. The antibody secreted in the culture medium of cells infected with the recombinant baculovirus was purified on protein A Sepharose column.
PC1: Control plasmid, plasmid containing the kappa light chain gene, PC2: Control plasmid, plasmid containing the γ1 heavy chain gene, R1-3, recombinant baculovirus 1, 2 and 3, MW: size marker.

Figure 10:
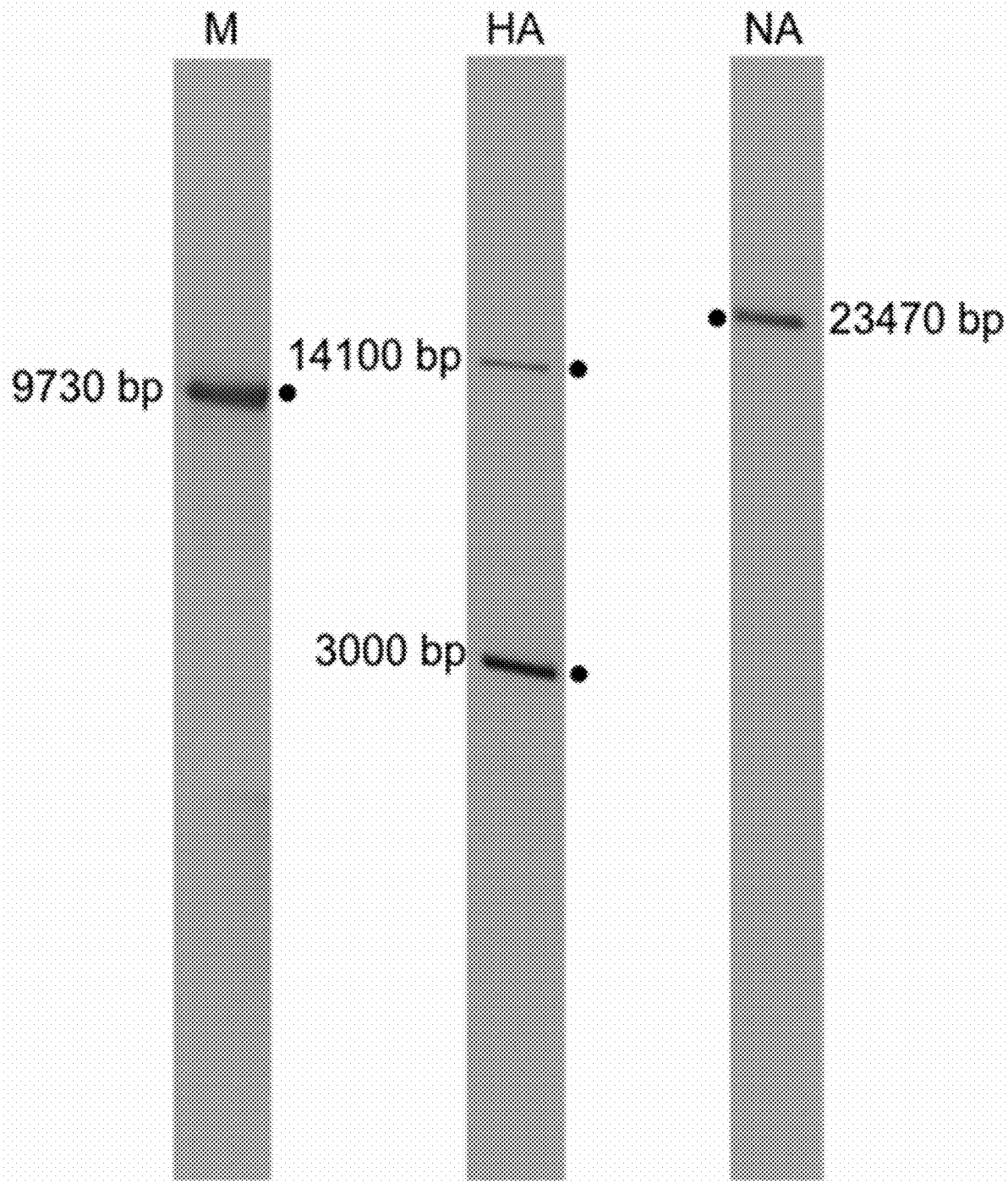

FIG. 10 is the Southern blot analysis of the genome of a triple recombinant virus expressing influenza virus M, HA and NA proteins.

Legend:
M: influenza virus gene encoding the matrix protein.
HA: influenza virus gene encoding hemagglutinin.
NA: influenza virus gene encoding neuraminidase.
bp: DNA fragment size expressed in base pairs.

FIG. 11 is a diagram illustrating in A the structure of the bispecific antibody and in B the polyacrylamide gel electrophoresis analysis of the purified bispecific antibody on protein A Sepharose column.

Legend:
A: Schematic representation of the structure of the bispecific antibody. L1: antibody 1 light chain; L2, antibody 2 light chain.
B: Purified bispecific antibody, analysed by polyacrylamide gel electrophoresis. Proteins are revealed by silver staining. (1) electrophoresis under reducing conditions (SDS, 2-mercaptoethanol). (2) electrophoresis under non-reducing conditions. H: antibody heavy chain, L: antibody light chain, H2L4: composition of the bispecific antibody: 2 fused heavy chains linked by 4 disulphide bridges at 2 hinge regions+4 light chains (2 L1 chains+2 L2 chains) specifically matched to the corresponding VH1-CH1 and VH2-CH1 regions.

EXAMPLES

Example 1: Construction of a Replication-Deficient Baculovirus Genome in which 1 Gene Essential for Viral Replication is Non-Functional (BacMid 1)

BacMid 1 has the deletion of a gene essential for viral replication, the 1629 gene.

1.1. Integration of the Bacterial Origin of Replication in a Baculovirus Genome

This operation is performed in the insect cell.

The bacterial Mini-F origin of replication was introduced into the polyhedrin locus of the baculovirus AcMNPV genome by homologous recombination in Sf9 (*Spodoptera frugiperda*) insect cells. To that end, the cells were transfected with (i) a PH transfer vector (pVT/Mini-F KanR) in which the ph gene sequence was replaced by a DNA fragment carrying the Mini-F+a bacterial expression cassette conferring Kanamycin resistance (KanR), and (ii) a baculovirus AcMNPV genome (baculovirus isolated from the lepidoptera *Autographa californica*). The generated baculoviruses were purified by the lysis plaque technique and then characterized to confirm that they had in fact integrated the Mini-F and the KanR expression cassette. A baculovirus was selected and then transferred to *E. coli* EL350 bacteria, thus generating a first BacMid (BacMid 0, not deficient for viral replication in insect cells).

1.2. Deletion of the Essential 1629 Gene

A bacterial expression cassette conferring ampicillin resistance (AmpR) and having at 5' and 3' the MauBI restriction site—a site absent from the baculovirus AcMNPV genome—was integrated downstream of the KanR bacterial expression cassette by homologous recombination in *E. coli* EL350 bacteria. During this recombination, a DNA fragment encoding the 27 C-terminal amino acids of the 1629 protein was deleted, making the 1629 protein non-functional. The ampicillin resistance gene was then removed after MauBI digestion and re-ligation, thus generating BacMid 1. The baculovirus genome (i.e. BacMid 1) is thus replication-deficient in insect cells because a gene essential for viral replication (i.e. the gene encoding the 1629 protein) is non-functional. Bacteria containing BacMid 1 are hereinafter referred to as "*E. coli* EL350/BacMid1 bacteria".

FIG. 1 illustrates the steps for the preparation of BacMid 1.

Example 2: Construction of a Replication-Deficient Baculovirus Genome in which 2 Genes Essential for Viral Replication are Non-Functional (BacMid 2)

BacMid 2 has the deletion of 2 genes essential for viral replication, the 1629 gene and the gene encoding the viral DNA polymerase (DNAPol). From BacMid 1, deletion of the DNAPol gene was performed in *E. coli* EL350/BacMid1 bacteria after electroporation of a 4222 bp recombination fragment in which part of the genes encoding gp37 (240 amino acids) and DNAPol (466 C-terminal amino acids) has been deleted and replaced by a bacterial expression cassette for producing hygromycin B phosphotransferase (HygroR), thus conferring hygromycin resistance (HygroR). The HygroR gene was placed under the control of the bacterial EM7 promoter (from the commercial vector pSelect-Hygromcs, Invitrogen), the glms terminator was introduced downstream of the HygroR gene (Gay N.J. et al. Biochem J., 1986, 234, 111-117). Bacteria containing BacMid2 (*E. coli* EL350/BacMid2) were selected for their resistance to hygromycin. The baculovirus genome (i.e. BacMid 2) is replication-deficient in insect cells because two genes essential for viral replication (i.e. the gene encoding the 1689 protein and the gene encoding DNAPol) are non-functional.

FIG. 2 is a diagram illustrating the step of deletion of DNAPol for the preparation of BacMid 2.

Note: BacMid 2 can be used to produce a single protein (see Example 4). It is sufficient to have two transfer vectors, one providing the exogenous gene to be produced and all or part of the deleted gene 1 and the other providing the wild-type gene corresponding to the deleted gene 2. Both deleted genes are repaired during homologous recombination.

Example 3: Construction of a Replication-Deficient Baculovirus Genome in which 3 Genes Essential for Viral Replication are Non-Functional (BacMid 3)

BacMid 3 has the deletion of 3 essential genes, 1629, DNAPol and gp64.

From BacMid 2, deletion of the gp64 gene was performed in *E. coli* EL350/BacMid2 bacteria after electroporation of a 3260 bp recombination fragment in which the entire cathepsin gene plus 779 bp of the sequence encoding 259 aa of chitinase and part of the gp64 gene, deletion of 566 bp encoding 188 amino acids, was replaced by a bacterial expression cassette conferring zeocin resistance (Drocourt et al., Nucleic Acids Research, vol. 18 no. 13, 1990). The Zeocin® gene derived from the commercial plasmid pCR®-Blunt (Invitrogen) was placed under the control of the bacterial T5N25 promoter, derived from phage T5 (Gentz and Bujard, *J. Bacteriology*, vol. 164 no. 1, 1985) and followed by the rrnBT1 transcription terminator (*E. coli* ribosomal RNA operon T1 terminator) (Kwon et al., *J Biol. Chem.*, vol. 274 no. 41, 1999). Bacteria containing BacMid3 (*E. coli* EL350/BacMid3) were selected for their resistance to Zeocin. The baculovirus genome (i.e. BacMid 3) is replication-deficient in insect cells because three genes essential for viral replication (i.e. the gene encoding the 1689 protein, the gene encoding DNAPol and the gene encoding gp64) are non-functional.

FIG. 3 is a diagram illustrating the step of deletion of gp64 for the preparation of BacMid 3.

Example 4: Use of BacMid 2

A transfer vector, pVT/gp37, was constructed to be able to generate recombinant baculoviruses expressing 2 exogenous genes. To that end, the EcoRI F fragment of the baculovirus AcMNPV genome containing the gp37 gene and the DNAPol gene was cloned into a bacterial plasmid, pUC, thus generating pUC/gp37.

This plasmid was then modified as follows: a large part of the gene encoding gp37 was deleted (724 bp), the ATG initiator was mutated and replaced by two unique restriction sites, XbaI and AvrII, allowing integration of an exogenous gene under the control of the natural gp37 promoter. These modifications thus led to transfer vector pVT/gp37.

Sf9 cells were transfected by lipofection with transfer vectors pVT/PH and pVT/gp37 loaded with the exogenous genes and the BacMid 2 DNA. The viruses generated after homologous recombination were cloned by the lysis plaque method. Production of the recombinant protein was verified by a suitable method (e.g. ELISA, Western blot, enzyme assay). The genome of the recombinant viruses was verified by Southern blot and the sequence of the exogenous gene integrated into the viral genome was verified by sequencing after PCR amplification.

FIG. 4 is a diagram illustrating transfer vector pVT/gp37 for the expression of a gene X (where X is a gene different from the gene encoding the heavy chain of an antibody).

The recombinant baculovirus genomes generated after homologous recombination between BacMid2 and the transfer vectors no longer express gp37 (protein non-essential for viral replication).

For the viral DNA to be repaired in both BacMid 2 loci, a second recombination must take place with a PH transfer vector optionally loaded with an exogenous gene. In all cases, the baculovirus genome DNA will be repaired and therefore infectious.

It will also be possible to use the pVT/PH containing a wild-type sequence, i.e. containing the wild-type (unmodified) expression cassette leading to the production of polyhedrin. The pVT/PH may also be "empty", i.e. containing neither an exogenous gene nor the polyhedrin gene.

FIG. 5 is a diagram illustrating the construction and use of PH transfer vector pVT/PH for the expression of an exogenous gene X (where X is an exogenous gene different from the gene encoding a light chain of an antibody).

Expression of the Heavy Chain of an Antibody.

Construction of a specific pVT/gp37, pVT/gp37-CY1

This transfer vector contains the following expression cassette:

Wild-type P10 viral promoter (SEQ ID NO: 1)
DNA sequence encoding a human immunoglobulin signal sequence (secretion sequence)
2 unique restriction sites for phase cloning of the variable region (VH) of the antibody (region that gives the specificity of the antibody)
DNA sequence that encodes an epsilon, mu, or alpha constant region of human IgG (¥1-4).

FIG. 6 is a diagram illustrating the construction and use of transfer vector pVT/gp37Cγ1 for the expression of the heavy chain of an antibody.

Expression of the Light Chain of an Antibody.

Construction of a specific pVT/PH-VL. This transfer vector contains the following expression cassette:

P10 viral promoter P10S1B (SEQ ID NO: 2)
DNA sequence encoding a human immunoglobulin signal sequence (secretion sequence)
2 unique restriction sites for phase cloning of the variable region (VL) of the antibody (region that gives the specificity of the antibody)
DNA sequence that encodes a kappa (κ) or lambda (l) light chain constant region of human IgG.

FIG. 7 is a diagram illustrating the construction and use of transfer vector pVT/PHCK for the expression of the light chain of an antibody.

Example 5: Use of BacMid 3

A transfer vector, pVT/Chit-Cath, was constructed to be able to generate recombinant baculovirus genomes expressing 3 exogenous genes.

The BstXI-XbaI fragment from the EcoRI E and H regions of the baculovirus AcMNPV was cloned in a pUC plasmid. An EcoNI-EcoRI deletion of 1175 bp inactivates the genes encoding chitinase (chiA), non-essential in vitro, and cathepsin (v-cath), also non-essential. The addition of an XbaI site between the EcoNI and EcoRI sites makes it possible to integrate an exogenous gene. These modifications thus led to transfer vector pVT/Chit-Cath. Sf9 cells are transfected by lipofection with transfer vectors pVT/PH, PVT/gp37 and PVT/chitCath loaded with the exogenous genes and the BacMid 3 DNA. The viruses generated during homologous recombination were cloned by the lysis plaque method. Production of the recombinant protein was verified by a suitable method (ELISA, Western blot, enzyme assay, etc.). The genome of the recombinant viruses was verified by Southern blot and the sequence of the exogenous gene was verified after PCR amplification.

FIG. 8 is a diagram illustrating the construction of vector pVT/Chit-Cath and its homologous recombination with BacMid 3.

Example 6: Production of an Anti-CD4 Monoclonal Antibody (13B8II) Using BacMid 2

CDNAs encoding the VH and VL regions of the antibody were integrated into transfer vectors PVT/PH-CK and pVT/gp37-Cy1, respectively. Recombinant baculoviruses were generated after homologous recombination between the 2 pVTs and BacMid 2 DNA from Example 4:
  cDNA encoding the VL region of the antibody was introduced into pVTPH/Ck which recombines with the PH/1629 region of BacMid2,
  cDNA encoding the VH region of the antibody was cloned into pVT/gp37-Cy1 which recombines with the gp37 region of BacMid2.

Sf9 cells were transfected by lipofection with BacMid 2 and the 2 transfer vectors obtained in Example 4 and incubated for 4 days at 28° C. Culture supernatants were collected and the recombinant baculoviruses generated, secreted in the culture medium, were cloned by the lysis plaque technique.

The organization of the genome of the recombinant baculoviruses was verified by Southern blot (see FIG. 9) and the integrated exogenous genes (i.e. VL and VH) were verified after PCR amplification, cloning and sequencing.

Example 7: Use of BacMid 3 for the Production of Virus-Like Particles (VLPs)

Production of Influenza VLPs

To produce these VLPs, the 3 genes of the influenza virus, M, HA and NA, were co-expressed.

These 3 genes were integrated into the three transfer vectors necessary to recombine with BacMid 3 from Example 5:
  The M gene was introduced into transfer vector pVT/PH as described in FIG. 5.
  The HA gene was introduced into transfer vector pVT/gp37 as described in FIG. 4.
  The NA gene was introduced into transfer vector pVT/Chit/Cath as described in FIG. 8.

Sf9 cells were transfected by lipofection with BacMid 3 and the 3 transfer vectors obtained above, then incubated for 4 days at 28° C. The recombinant baculoviruses generated and secreted in the culture supernatant were cloned by the lysis plaque method.

The organization of the genomes of the recombinant baculoviruses was verified by Southern blot (see FIG. 10) and the integrated genes were verified after PCR amplification, cloning and sequencing. The Southern blot was performed on genomic DNA of the recombinant virus expressing the 3 influenza virus proteins HA, NA and M to detect cDNA encoding the integrated M, HA and NA proteins. The membranes were hybridized with probes specific to these 3 genes.

Example 8: Use of BacMid 3 for the Production of Bispecific Antibodies

The bispecific antibody constructed according to the patent (PCT/IB2012/053482) consists of a heavy chain composed of the VH+CH1+CH2+CH2+CH3 domains of an antibody 1, N-terminal fused to the VH+CH1 domains of an antibody 2. Mutations introduced at the interface of the CL and CH1 regions of antibody 1 promote correct matching between the VL1 and VL2 domains of light chains L1 and L2, which are produced separately, and the corresponding VH1 and VH2 domains. Production of this antibody requires simultaneous and equal production of 3 chains, the fused heavy chain, light chain L1 and light chain L2.
  cDNA encoding light chain L1 was introduced into transfer vector pVT/PH as described in FIG. 5.
  cDNA encoding light chain L2 was introduced into transfer vector pVT/gp37 as described in FIG. 4.
  cDNA encoding the fused heavy chain was introduced into transfer vector pVT/Chit-Cath as described in FIG. 8.

FIG. 11 is a diagram illustrating in A the structure of the bispecific antibody and in B the polyacrylamide gel electrophoresis analysis of the bispecific antibody purified on protein A Sepharose column.

The invention claimed is:

1. A process for preparing, in an insect cell, a recombinant baculovirus comprising n exogenous gene expression cassettes each to be expressed at a different locus, the process comprising introducing a replication-deficient recombinant baculovirus genome and n transfer vectors into an insect cell and thereby allowing multiple homologous recombination between:
   a) a replication-deficient baculovirus genome in which n genes essential for viral replication are distributed in n different loci of the viral DNA and are all non-functional, wherein the n non-functional genes essential for viral replication are each adjacent to a different gene non-essential for viral replication; and
   b) n transfer vectors each restoring the function of only one of the n non-functional genes essential for viral replication and each comprising:
      i) a nucleotide sequence that restores the function of only one of the n non-functional genes essential for viral replication, and
      ii) only one of the n exogenous gene expression cassettes, each of the n expression cassettes to be expressed at a different locus,
      the set of nucleotide sequences i) of the n transfer vectors being able to restore replication of the replication-deficient baculovirus genome;
wherein all n being the same and being an integer at least equal to 2, and
wherein the replication-deficient baculovirus genome and the n transfer vectors are all present in the same insect cell simultaneously, prior to the multiple homologous recombination with all n transfer vectors.

2. The process according to claim 1, wherein the genes essential for viral replication are selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147) and lef-2 (ORF6).

3. The process according to claim 1, wherein the gene non-essential for viral replication is selected from Ph (ORF 8), ORF11, ORF13, egt (ORF15), v-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96), he65 (ORF105), ORF108, ORF110, cathepsin (ORF127), p24 (ORF129), pp34 (ORF131), ORF134, ORF145, odv-e56 (ORF148) and ORF5.

4. The process according to claim 1, wherein the n exogenous gene expression cassettes each recombine with a gene non-essential for viral replication adjacent to a non-functional gene essential for viral replication.

5. The process according to claim 1, wherein the transfer vectors comprise, on either side of one of the n exogenous gene expression cassettes, flanking sequences homologous to the replication-deficient baculovirus genome.

6. The process according to claim 5, wherein the flanking sequences have a length ranging from 10 bp to 10 kb.

7. The process according to claim 1, wherein the insect cell is selected from the group consisting of: Sf9, Sf21, Tn5-b14, baculovirus AcMNPV-sensitive lepidopteran cell lines, and Sf21 lines.

8. The process according to claim 1, wherein the replication-deficient baculovirus genome is obtained from a baculovirus genome selected among or derived from the group of the baculovirus genomes consisting of: BmNPV, AcMNPV, ApNPV, BsSNPV, CMNPV, EOSNPV, HaNPV, HzNPV, LdMNPV, MbMNPV, OpMNPV, SlMNPV, SeMNPV and TeNPV.

9. The process according to claim 1, wherein n is an integer ranging from 2 to 30.

10. The process according to claim 1, wherein the replication-deficient baculovirus genome is obtained from the baculovirus genome of AcMNPV.

* * * * *